United States Patent [19]
Clark

[11] Patent Number: 4,761,375
[45] Date of Patent: Aug. 2, 1988

[54] HUMAN INTERLEUKIN-2 CDNA SEQUENCE

[75] Inventor: Steven C. Clark, Winchester, Mass.

[73] Assignee: Genetics Institute, Inc., Cambridge, Mass.

[21] Appl. No.: 849,234

[22] Filed: Apr. 7, 1986

Related U.S. Application Data

[63] Continuation of Ser. No. 608,228, May 8, 1984, abandoned.

[51] Int. Cl.[4] .................. C12N 5/00; C12N 15/00; C12N 1/20; C12N 1/00
[52] U.S. Cl. .................. 435/240.2; 435/172.3; 435/253; 435/320; 935/10; 536/27
[58] Field of Search .................. 435/68, 172.3, 240, 435/253, 317, 240.2, 320, 10; 536/27

[56] References Cited

U.S. PATENT DOCUMENTS 4,438,032 3/1984 Golde et al. .................. 435/68
4,530,787 7/1985 Shaked et al. .................. 435/68

OTHER PUBLICATIONS

Taniguchi et al., Nature vol. 302, pp. 305–310, Mar. 24, 1983.
Maeda et al., Biochem and Biophys Res. Commun., vol. 115, pp. 1040–1047, Sep. 30, 1983.
Devos et al., Nucleic Acid Res., vol. 11, pp. 4307–4323, Jul. 1983.

Primary Examiner—Alvin E. Tanenholtz
Attorney, Agent, or Firm—Bruce M. Eisen; Mary E. Bak; Ellen J. Kapinos

[57] ABSTRACT

The mRNA of a distinct human Interleukin-2 concentrated from a plasma source lead to the production and cloning of its cDNA and the elucidation of its sequence and that of the mature protein. Transfer vectors for production of such Interleukin-2 are disclosed along with useful intermediate expression products.

5 Claims, 8 Drawing Sheets

HUMAN INTERLEUKIN-2 CDNA SEQUENCE

This is a continuation of application Ser. No. 608,228, filed May 8, 1984 and now abandoned.

The T-cell growth factor (TCGF), also known as Interleukin-2(IL-2), is a lymphokine produced by lectin- or antigen-activated T-cells in mammals.

The structure and expression of a precursor protein coded by a cloned gene constructed from human mRNA for TCGF has been reported by Taniguchi et al., Nature, Vol. 302, 305–310 (March, 1983).

The present invention is based on the discovery and provision of a human TCGF distinct from that previously reported.

In the following text, as will be evident to those skilled in art, the description refers to systems containing or involving nucleotide or amino acid sequences of either or both the previously reported human TCGF and the human TCGF provided by the invention. Such systems are referred herein by the designation "mTCGF." The designation "aTCGF" is used herein with specific reference to the human TCGF discovered and provided by the invention.

The following definitions are used throughout this text for purposes of clarification and/or shortening the necessary description:

Cloning vehicle, vector, transfer vector and the like—all refer to non-chromosomal DNA (double stranded unless otherwise indicated) and capable of replication (by reason of containing an intact replicon) when placed within a host, e.g. animal cells or a microorganism. However, the term cloning vehicle is often used when the purpose is primarily cloning (multiplication) and not expression, and the term transfer vector, when used, generally indicates a recombinant construct containing heterologous DNA (more particularly the whole or portion of a coding sequence whose expression is ultimately desired) and prepared in furtherance of the objectives of the invention. The term vector is used in the generic sense to cover plasmids, bacteriophages and other similarly useful vehicles, such as those used as starting materials herein, but is also used to refer to recombinant derivatives thereof. Hence, the terms may be used interchangeably and even overlap with regard to the above indicated more particular meanings usually desired to be emphasized in their use.

Transcription Control System—used herein with reference to the structure of recombinant vehicles such as in a vector, transfer vector and the like, to denote a double-stranded DNA region or regions comprising at least the DNA construction operatively necessary to control transcription of ribosomal translatable mRNA in a host. The term is also intended to encompass all of the elements which may be included in a particular system for purposes of controlling, regulating and enhancing transcription. Such elements include without limitation those well known as promoters and operators (together the promoter-operator system), CAP binding sites, ribosomal binding site sequences, so-called "Nut sites" and enhancers. As will be understood, the elements minimally necessary to operatively effect tranticription will depend upon various factors, particularly the host in which transcription is to be effected. For example, an operator may depend upon repressor protein produced by a regulator but the regulator may be located in the chromosome of the host in which the transfer vector is placed (e.g. by transformation) in which case such regulator will not by definition form a part of the transcription control system of the vector. Similarly, a sequence coding for a ribosomal binding site in order to produce translatable mRNA may be necessary only for certain hosts, such as bacterial hosts in general.

Recombinant Operon—a double-stranded DNA segment comprising a transcription control system and a sequence coding for aTCGF under its control.

Expression—is intended to be generic to the independent processes of transcription and translation, i.e. the production of mRNA and the production of a protein from the mRNA.

The above and other objects of the invention will be evident from the following description and the accompanying drawings in which:

FIG. 1 represents the overall cloning strategy by which isolated poly-(A) mRNA is enzymatically converted into duplex cDNA for recombinant integration into the plasmid pBR322 to produce a plurality of cloning vehicles pBR322-cDNA which are used to transform bacteria to obtain a library of clones which was screened to find clones transformed with a cloning vehicle containing the cDNA of the mTCGF messengers, said desired cloning vehicle being also designated pBR322-mTCGF.

FIG. 2 represents the strategy for obtaining by duplex DNA degradation segments of the mTCGF cDNA from pBR322-mTCFG for sequencing by the M13 dideoxy sequencing method. Four of the five segments obtained as a result of this procedure were sequenced as shown in FIG. 3 (see below).

FIG. 3 represents the strategy for obtaining by restriction endonuclease cleavage sections of the mTCGF cDNA duplex from pBR322-mTCGF for sequencing by the M13 dideoxy sequencing method. FIG. 3 also indicates the sequencing of an additional segment obtained using a 5' 17 mer primer. In addition, FIG. 3 also depicts the sequencing of four of the five degraded cDNA sections obtained by the method represented by FIG. 2.

Table A, below, depicts the amino acid sequence of aTCGF and the nucleotide sequence its cDNA segment which embodies the coding region for the mature protein, a signal peptide region and upstream (5') and downstream (3') untranslated regions coded for by the natural gene. Amino acids are designated by conventional abbreviations and numbered at intervals above such designations. The nucleotides in the sequence are numbered below their designation in units of fifty with a dot placed at every interval of ten nucleotides. Certain restriction sites within the sequence are also identified.

As a source material for the mRNA of the mTCGF there was employed a mixture of four (4) human plasmaphersis by-products made available by the Red Cross.

Figure 1:
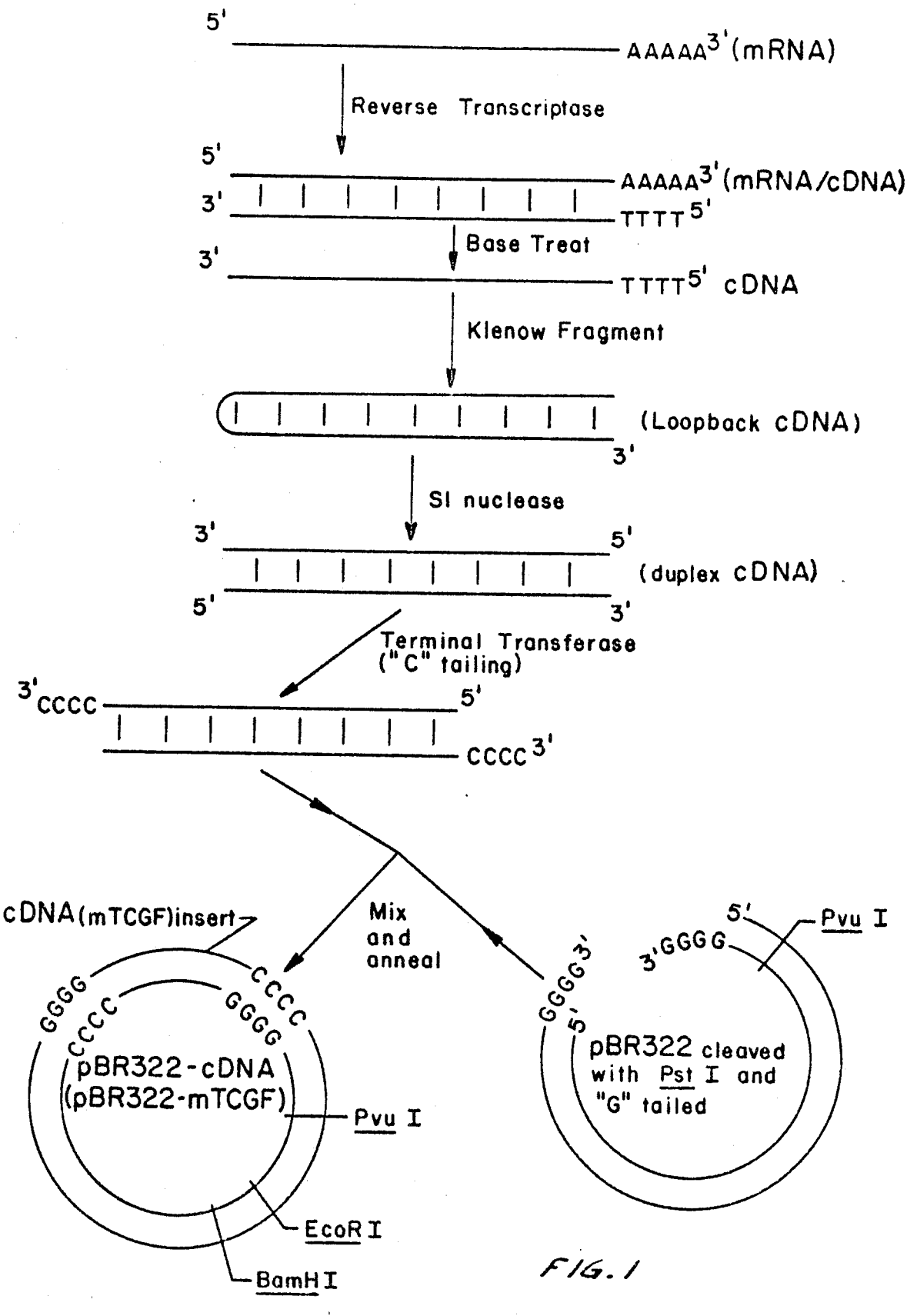

As exemplified hereinafter, the plasmaphersis by-product sample may be cultured in vitro and induced with a mitogen and thus multiply levels of mTCGF and the mRNA thereof. The cells may then be lysed to free their cytoplasmic RNA content and the mRNA may then be isolated using an oligo dT cellulose column. The presence of desired mRNA for mTCGF in the collected mRNA mixtures may then be ascertained using a standard *Xenopus laevis* translation system and suitable assay for T-Cell Growth Factor activity. Having thus found significant levels of mRNA for mTCGF in the collected mRNA mixture, such mixture becomes useful for attempting the construction, isolation and identification of mTCGF producing DNA duplexes from the mRNA. This may be accomplished by first forming double stranded cDNA from the total mRNA in the mixture. As outlined in FIG. 1, treatment of the mRNA mixture with reverse transcriptase (to form mRNA/cDNA) followed by a base (to separate the cDNA) and then by the large fragment of DNA polymerase I (Klenow Fragment), results in the production of double stranded hairpin loopback forms of cDNA and the hairpin loops may be successfully cleaved by S1-nuclease. The resulting duplex cDNA may be then cloned by integration of the cDNA into any of a variety of vectors, such as a plasmid, such as the plasmid pBR322 which may be used to form a plurality of cloning vehicles pBR322-cDNA, as shown in FIG. 1. The integration of the cDNA of unknown structure into the cloning vector may be facilitated by homopolymeric tailing of the ends of the cDNA and complementary homopolymeric tailing of the ends of the cloning vector which has been linearized by restriction cleavage, such tailing being desirably selected to reestablish restriction sites upon integration of the cDNA into the linearized vector. Thus, as shown in FIG. 1, the integration of the obtained cDNA into the plasmid pBR322 was effected by homopolymeric "C" tailing of the 3' ends of cDNA and complementary homopolymeric "G" tailing of the 3' ends of the plasmid pBR322 which had been cleaved with the restriction endonuclease Pst I to form cohesive termini. The "G" tailing of the 3' ends from such Pst I cleavage will lead to the reestablishment of Pst I cleavage sites in the transfer vector formed on integrating the "C" tailed cDNA into the "G" tailed linearized plasmid, thereby enabling the convenient removal of the inserted cDNA (mTCGF) segment as later desired from the cloning vehicles pBR322-cDNA (pBR322-mTCGF).

The resulting mixture of cloning vehicles pBR322-cDNA are used to transform a suitable replication host, such as *E. Coli* (e.g. strain MC1061). Following standard procedures, the resulting transformants are dispersed on filters and cultured in the presence of antibiotic (to eliminate non-transformed bacteria) to obtain a library of individual clones. Such library (following replica plating) can be employed to screen for the candidate clone(s) containing a cDNA insert with the desired coding sequence.

The screening for the desired candidate clone(s) may be effected employing standard colony hydridization procedures along with a suitable identification means capable of locating the candidate clones. Such identification means may be $^{32}P$ labelled oligonucleotides of reasonable length and useful as probes by reason of each nucleotide therein being able to attach itself by hydrogen bonding to its complementary base pair nucleotide in the cDNA segment sought to be found, it being necessary that the structures be substantially fully complementary over their entire length. Two such oligonucleotide probes each of 17 nucleotides and having the structures:

d(G-C-A-C-C-T-A-C-T-T-C-A-A-G-T-T-C), and d(C-T-G-A-T-T-A-A-G-T-C-C-C-T-G-G-G)

were found in colony hydridization to both hydridize (bind) with six (6) different colonies out of about 40,000 colonies in the work detailed hereinafter in Example 1.

Figure 3:
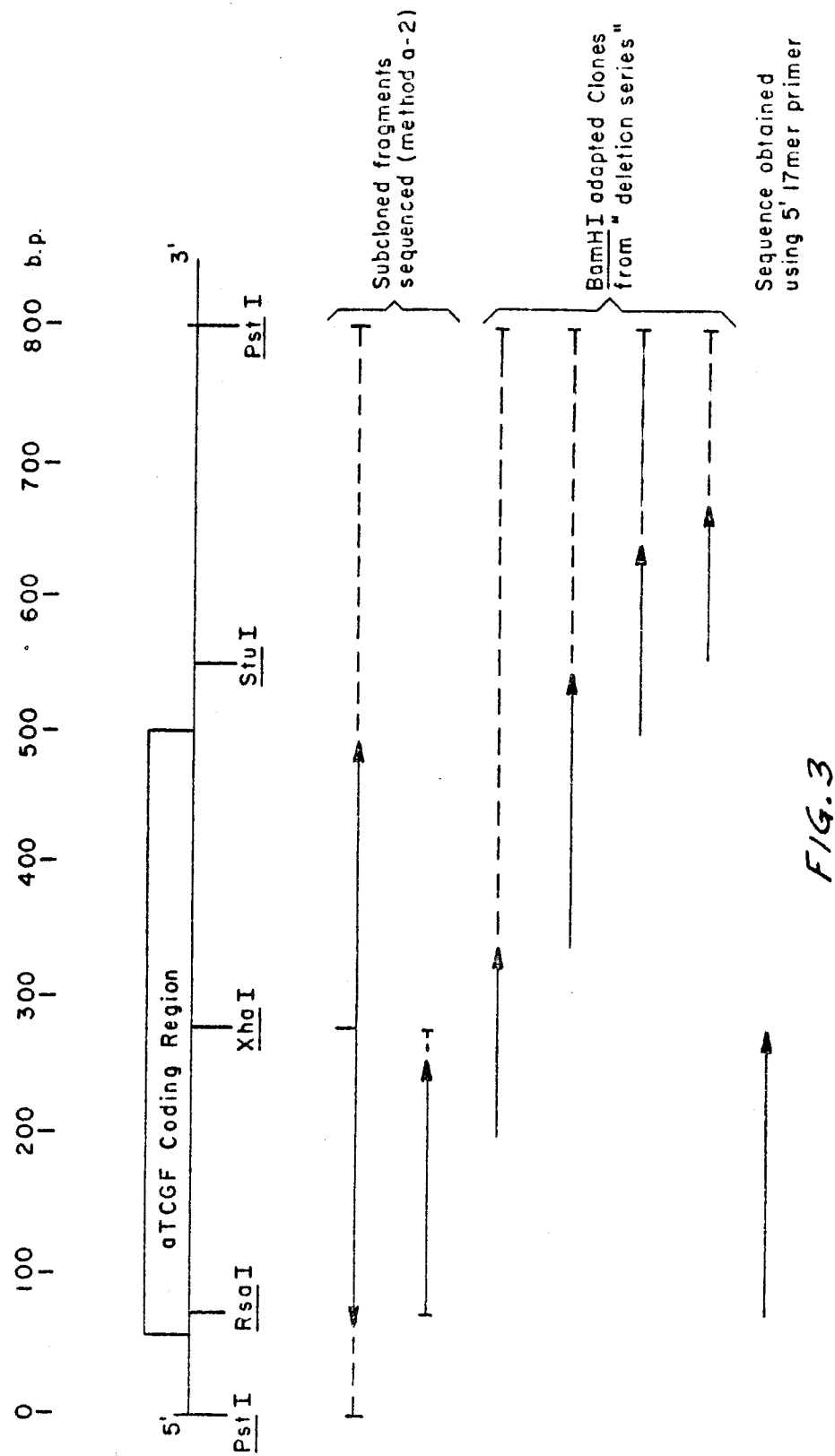
Figure 4:
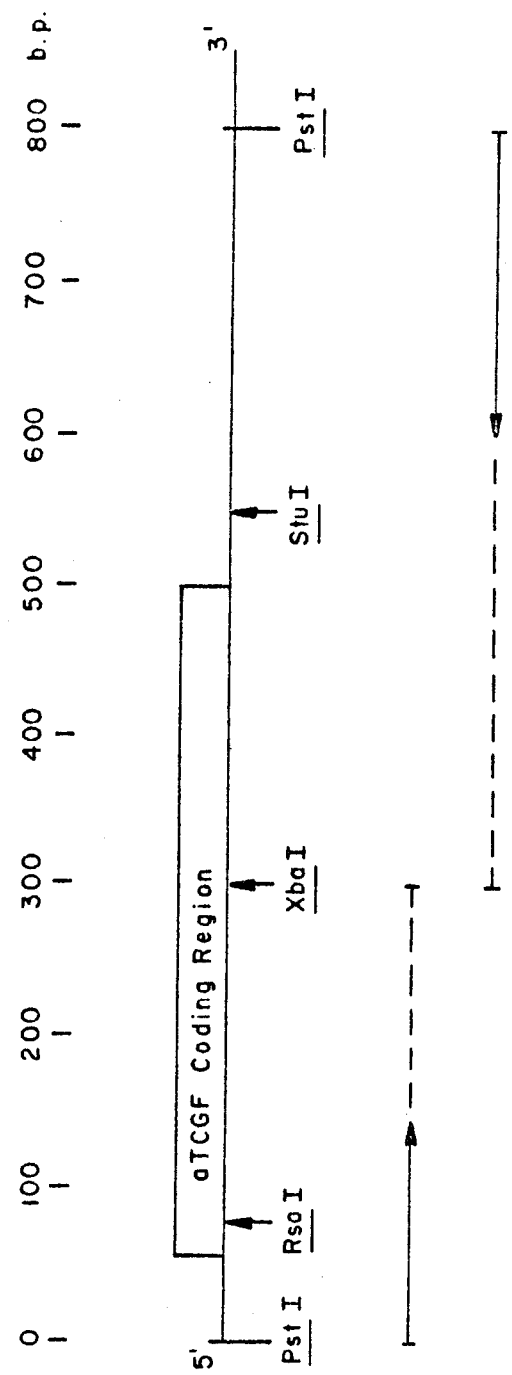
FIG. 4 represents a strategy for obtaining by restriction endonuclease cleavage sections of the mTCGF cDNA duplex from pBR322-mTCGF for sequencing by the Maxam-Gilbert method.

The discovery involved in the present invention began as a result of sequencing to elucidate the nucleotide sequence of the cDNA inserts in the pBR322-mTCGF in four of the six candidates identified as indicated above. As later herein detailed, the cDNA inserts of such four pBR322-mTCGF were sequenced employing (to insure confidence) a combination of dideoxy DNA sequencing and Maxam-Gilbert specific chemical degradation DNA sequencing. The strategies represented in FIG. 2 (DNA degradation) and FIG. 3 (restriction cleavage) were both employed for obtaining cDNA fragments for dideoxy sequencing. FIG. 4 shows the restriction cleavage strategy for obtaining fragments for Maxam-Gilbert sequencing. The results of such sequencing are set forth below in Table A and provided the discovery that one of the four cDNA inserts contained a sequence coding for a mature protein (designated aTCGF) which is distinct in its sequence from the currently known T-Cell Growth Factor. The transfer vector pBR322-mTCGF which contained the sequence coding for the distinct aTCGF is designated pBR322-aTCGF herein. *E. coli* MC1061 transformed with said pBR322-aTCGF, as produced as described in the exemplification hereinafter, was also designated *E. coli* MC1061-pTCGF-11 when placed on deposit with the American Type Culture Collection with the assession number ATCC 36973.

TABLE A

Sequence of aTCGF cDNA Clone.

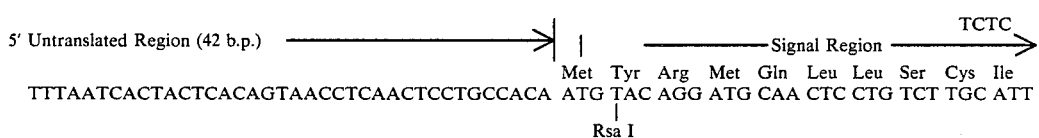

TABLE A-continued
Sequence of aTCGF cDNA Clone.

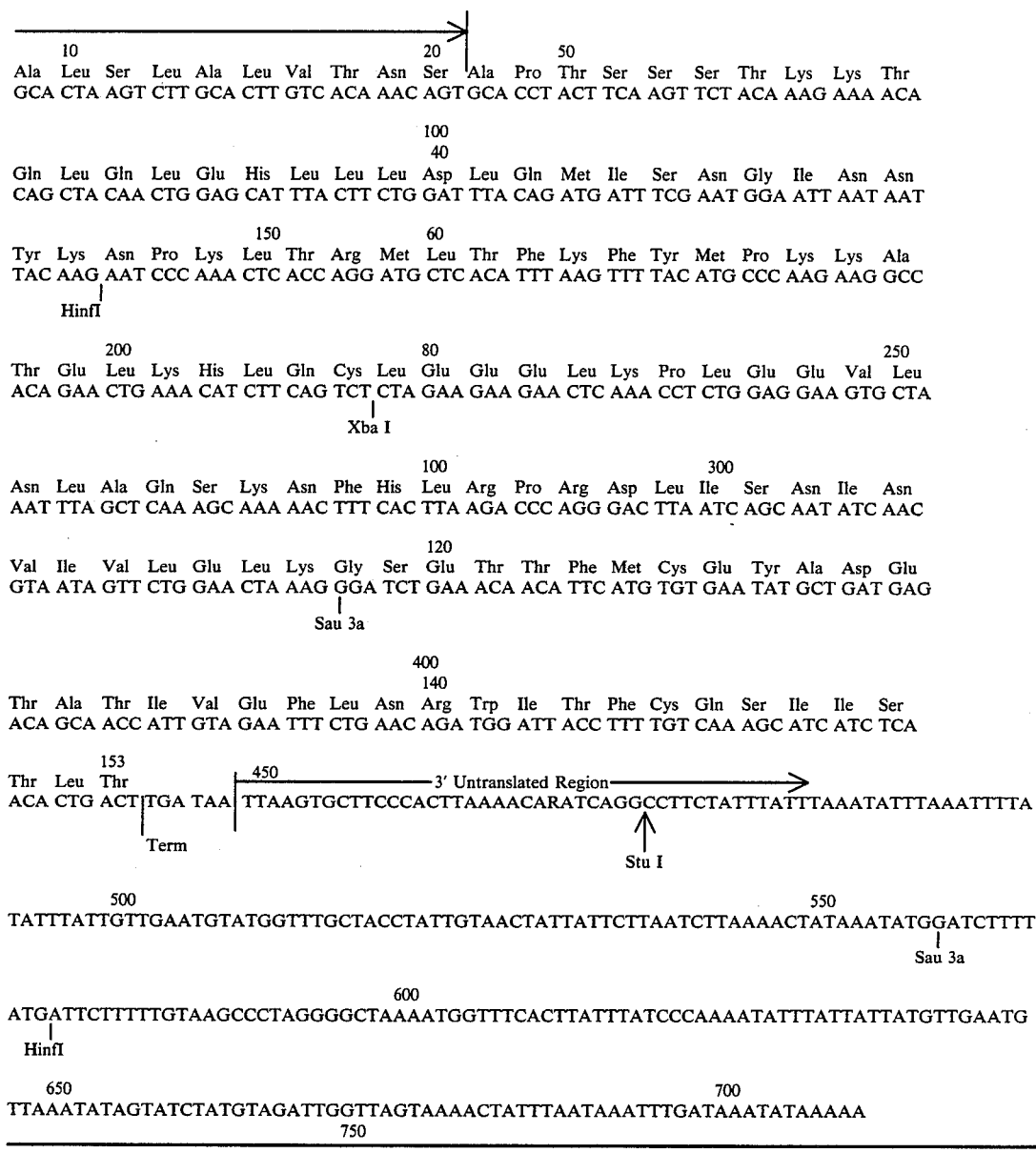

In Table A, above, the first nucleotide triplet coding for Met is assigned the number 1 and the identification and numbering of amino acids ends with the codon for Thr at position 153 in view of the immediately following pair of stop signals (TGA and TAA). As might be expected, the sequence analysis indicated that the nucleotide chain of the mRNA transcribed by the aTCGF gene region is of far greater length than the nucleotide length of the coding region for the mature aTCGF protein. Hence, the analysis indicated initially that the mature aTCGF protein could have as many as 153 amino acids but from further efforts described hereinafter it is indicated that the mature aTCGF protein is composed sequentially of the amino acids numbered 21 to 153, inclusive, in Table A. The sequence also showed upstream from the first Met codon a TAA termination signal in phase with the first Met codon, thus indicating that the cDNA obtained included the whole of the aTCGF sequence. Hence, the aTCGF gene region found in the cDNA begins with an upstream (5') untranslated section of 42 base pairs followed sequentially by a signal peptide sequence of 60 base pairs, the mature protein coding sequence having 459 base pairs, a pair of stop codons totalling 6 base pairs and a substantial downstream (3') untranslated section. Also shown in Table A are various endonuclease restriction sites indicated by the revealed sequence.

The invention thus provides transfer vectors containing a coding sequence for aTCGF whereby such sequence may be cloned. It also provides transfer vectors comprising a aTCGF coding sequence whereby the sequence may be expressed and production of the aTCGF protein achieved. Such transfer or expression vectors may be produced basically by placing at least the sequence coding for aTCGF in a vector such that the coding sequence is located under transcription control of a transcription control system in the transfer vector. The resulting vehicle will be a transfer vector comprising a recombinant operon comprising a coding sequence for aTCGF. By reason of its intact replicon the transfer vector will also be adapted to be suitable for replication and also for expression in a pre-selected host, e.g. animal cells or microorganisms, such as yeast or bacteria. A wide variety of vectors are available for constructing such expression vectors. In general, the particular vector to be used will depend, in addition to the matter of the host, upon various other known factors, but generally in accord with an overall strategy for expression. Commonly, many such vectors are also recombinant derivatives of other vectors, for example, sections from two or more plasmids may be combined or sections from plasmids and bacteriophages may be combined, thus providing certain desired properties while omitting sections considered less desirable for a particular purpose. The transcription control system and/or various elements thereof may be obtained from various sources which are different than the source of other sections of the transfer vector, mainly in an effort to improve expression in particular hosts. A variety of promoters, promoter-operator systems, ribosome binding site sequences and other elements are known and may be used for this purpose.

In general, the sequence in an expression vector prior to or upstream from the codon for 21-Ala, the beginning of the mature protein, may vary depending upon certain factors such as the overall strategy for finally producing aTCGF including the host to be used for expression. Since the mature aTCGF begins with Alanine (21-Ala) rather than methionine (Met) which provides the translation initiation codon ATG in messenger RNA, it becomes in order to provide an ATG codon upstream from and in reading phase with the aTCGF coding sequence. Providing for the ATG codon at an upstream location from the 21-Ala may be effected utilizing an ATG already in a sequence comprising the aTCGF coding sequence, e.g. the aTCGF cDNA insert, or the same may be otherwise provided from an extraneous source such as the plasmid to the used for expression, provided that the ATG first appearing before the 21-Ala codon is in reading phase with the 21-Ala codon. In general, the aTCGF coding sequence will be followed by one or more codons to allow the production of a aTCGF protein which ends with last amino acid of the mature protein (153-Thr in Table A). This objective may be generally accomplished by having one or more translation termination codons immediately following the aTCGF coding sequence as represented by the sequence elucidated for the cDNA.

For purposes of producing aTCGF, the cDNA insert containing the aTCGF coding sequence as available in the cloning vector pBR322-aTCGF may be excised therefrom and utilized per se or in other various ways. Since the sequence analysis showed the cDNA to contain a nucleotide region upstream from the aTCGF coding sequence, a portion or the whole of this upstream section may be removed. Hence, the whole or a portion of untranslated region of some 42 base pairs may be removed. The specific embodiments herein described are merely illustrative of the manner in which the cDNA insert may be used to construct transfer vectors suitable for producing aTCGF.

Expression in animal cells was the initial objective for expression in order to finally clarify the sequence of the aTCGF protein in view of the presence of the apparent signal peptide sequence (for amino acids 1–20 in Table A), since the production of the protein encoded by the sequence in animal cells afforded the opportunity that the cell system would cleave away any leading signal peptide from a precursor protein product, thus yielding the mature protein.

Thus, as shown in FIG. 5, the cloning vehicle pBR322-aTCGF may be linearized by digesting with the endonuclease Pst I which also has the effect of liberating the aTCGF insert from the cloning vehicle. The resulting aTCGF cDNA segment contains about 800 base pairs and has a cohesive Pst I terminus at each end.

As also shown in FIG. 5, the ca 800 b.p. aTCGF cDNA segment is used to form an expression transfer vector by integrating the same into the plasmid pCVSVL which has been linearized by cleavage at its sole Pst I site. The plasmid pCVSVL is known and has been described, for example, by Kaufman et al, Molecular and Cellular Biology, November 1982, pages 1304–1319, the disclosure of which is incorporated herein by reference as regards the structure and properties of pCVSVL to the extent not described herein. The plasmid pCVSVL has its Pst I almost immediately downstream from its leftward reading (shown by arrow in the recombinant plasmid pCVSVL-aTCGF in FIG. 5) Adenovirus major late promoter (AdMLP) region. Immediately downstream from the Pst I site is the gene section from Dihydrofolate Reductase (DHFR) and the plasmid has two animal cell replicons (SV40or[i]) in the region of its three Xho I sites. As also evident from FIG. 5, the plasmid has a 5′-3′ splice site (SS). Hence, the plasmid pCVSVL is particularly suitable for expression in animal cells upon insertion of the desired coding sequence in the correct reading orientation to the AdMLP promoter region. The integration of the aTCGF sequence-containing segment into the Pst I site of pCVSVL plasmid forms the transfer vector pCVSVL-aTCGF (identified after cloning in *E. Coli*). Transfection of monkey COS-7 cells with pCVSVL-aTCGF led, after a 48–72 hour induction period, to an expression protein product which assayed positively for T-cell Growth Factor activity. Purification and sequence analysis of this protein product confirms the mature aTCGF product to be a polypeptide having the amino acid sequence 21–153 as set forth in Table A, and free N- and C-termini.

The expression of the aTCGF sequence and production of aTCGF in bacteria is represented in FIGS. 6 and 7. In the embodiment shown in FIGS. 6 and 7, the strategy is to employ a coding sequence in which the desired ATG codon is placed upstream and immediately adjacent the 21-Ala codon, whereby upon expression in a suitable transfer vector in bacteria at least a portion of the normally encoded precursor protein (-1)-Met-aTCGF will be produced and proteolytically converted to the mature aTCGF protein product. One manner of effecting the strategy of FIGS. 6 and 7 begins with the preparation of a aTCGF coding segment in which the first upstream codon is the codon (GCA) for the first amino acid (21-Ala) of the mature aTCGF protein. As represented in FIG. 6, such a coding segment may be produced from the aTCGF cDNA insert available between its Pst I insertion sites in the pBR322-aTCGF cloning vehicle. Cleavage of pBR322-aTCGF with Pst I provides the aTCGF-cDNA (ca 800 b.p.) insert which is then inserted at the Pst I site of a double stranded (ds) M13 vector, e.g. M13mp9, which has been obtained by transformation of E. Coli with the single stranded (ss) bacteriophage M13 vector and collecting the resulting ds form. Transformation of E. Coli with the resulting transfer vector dsM13-aTCGF by known procedures results in the cloning (multiplication) of the vector and the eventual discharge and recovery from the supernatant of a substantially single-stranded cyclic DNA (ssM13-aTCGF in FIG. 6 in which the single stranded remainder of the reestablished restriction cleavage sites are given in parenthesis) in which the coding strand of the aTCGF insert has been removed. Such single-stranded replica of the vector will be employed as a template for synthesis of a aTCGF coding segment which will begin at the codon for 21-Ala. For this purpose, a single stranded oligonucleotide of suitable length, e.g. a 17 mer (21-Ala primer-5' 17 mer in FIG. 6), is synthesized such that its sequence is complementary to the non-coding strand beginning at the codon for 21-Ala. The balance of the oligonucleotide is constructed such that each nucleotide thereof is complementary in series to the corresponding nucleotide in the template. Hence, a suitable 17 mer will have the structure 5' d(GCACCTACTTCAAGTTC). Mixing of the oligonucleotide with the single-stranded template (ssM13-aTCGF) results in the oligonucleotide hydridizing to the first 17 nucleotides of the template corresponding to the aTCGF coding sequence and beginning with the first template nucleotide complementary to the first nucleotide of the 21-Ala codon. Such hydrization effectively provides a primer site for synthesis of additional portions complementary to the template by treating with the Klenow fragment in the known manner. Such synthesis of the complementary strand is sufficiently effected or continued well beyond the BamHI site provided by the M13 vector. Treatment of the resulting product with the Nuclease S1 removes the remaining single stranded portions and the resulting DNA which is now linear is treated with the Klenow fragment with all four deoxynucleotides added to insure the formation of a aTCGF code-containing duplex which begins exactly with a blunt end coding for 21-Ala. The final aTCGF DNA duplex (aTCGF Gene Segment BE in FIGS. 6 and 7) is obtained by cleaving the linear DNA with BamHI which cleaves in the so-called M13 polylinker section adjacent to the reestablished Pst I where the aTCGF cDNA was inserted into the dsM13 vector. Hence, the final aTCGF coding duplex has a 5' blunt end beginning with the codon for Ala and at the other end a cohesive terminus from the BamHI cleavage.

Figure 6:
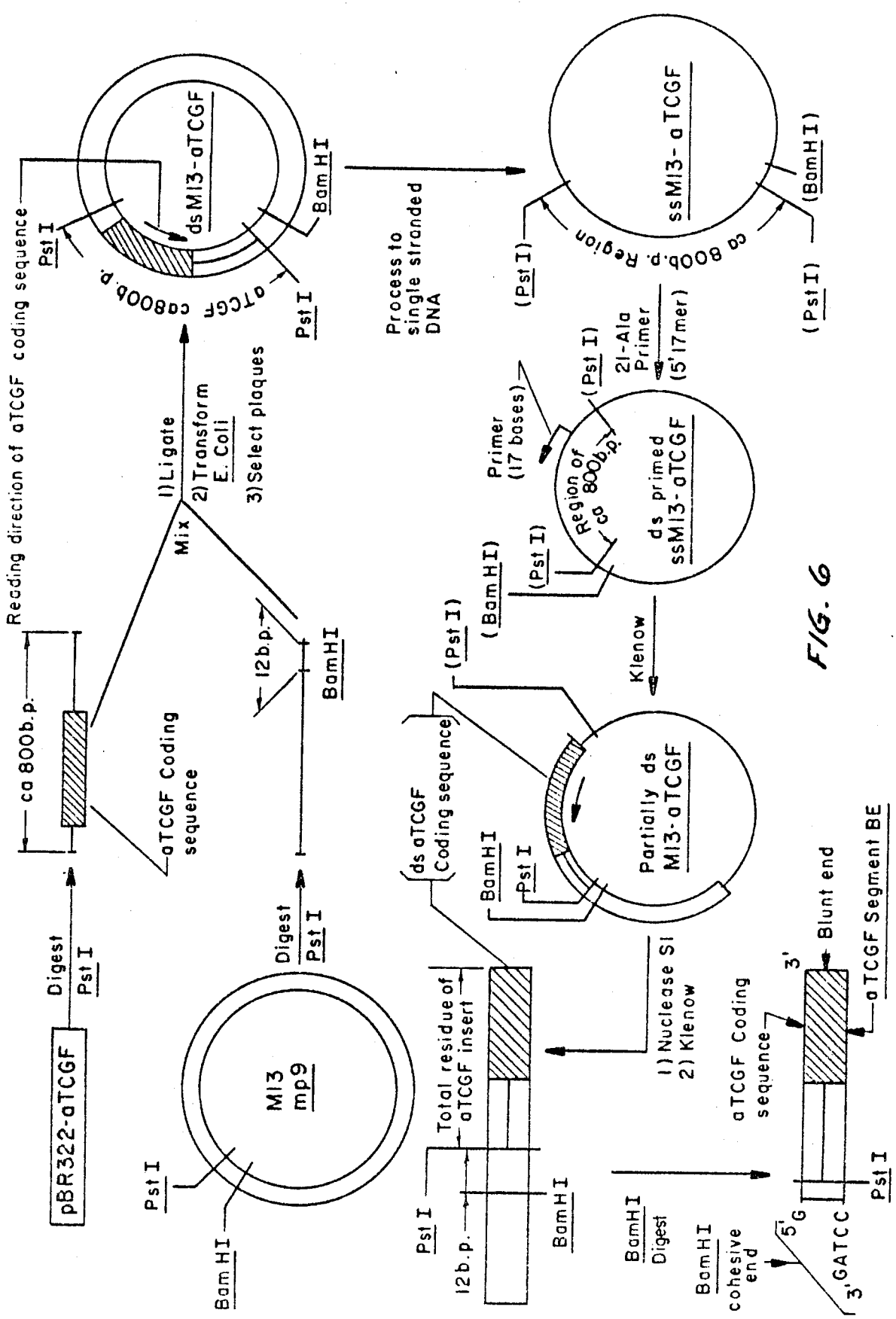
FIG. 6 shows the construction of an aTCGF coding segment useful for constructing a transfer vector pEVPL-aTCGF (FIG. 7, below) which is useful for producing aTCGF in bacteria.
Figure 7:
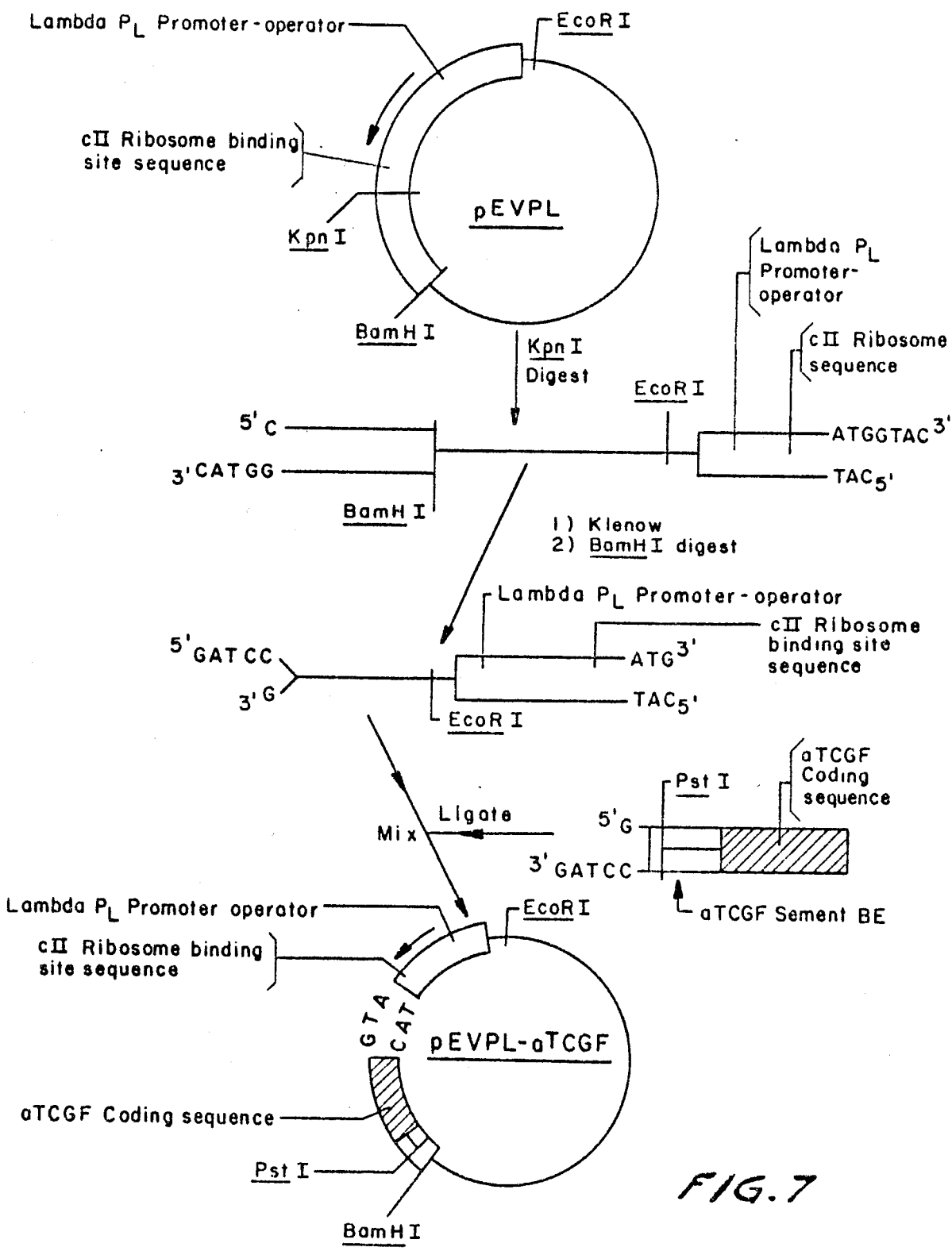
FIG. 7 shows the construction of the transfer vector pEVPL-aTCGF derived from the plasmid pEVPL and capable of producing aTCGF in bacteria.

In the strategy represented in FIGS. 6 and 7 the objective of having the initiation triplet ATG coding for Met at the beginning of the mature aTCGF coding sequence is accomplished by making the ATG available from the plasmid to be used to form the recombinant expression vector for transforming the bacterial host. As shown in FIG. 7, the desired ATG codon may be provided in the ultimate expression transfer vector for producing aTCGF by employing a plasmid such a pEVPL (shown in detail in FIG. 8). This plasmid has a lambda $P_L$ promoter-operator upstream from the cII ribosome binding site sequence that is immediately followed by a nucleotide section terminating in a Kpn I site. This section begins with the ATG translation initiation codon of the cII coding sequence (which otherwise has been removed) and the Kpn I site partially overlaps this desired ATG sequence (underlined below), said section with its actual Kpn I cleavage locations shown by arrows being:

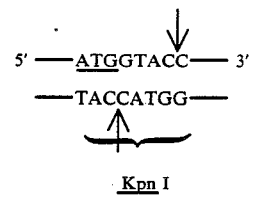

Kpn I

Cleavage of pEVPL with Kpn I creates a 3' GTAC overhang which can be readily trimmed back to the blunt ended G-C base pair terminal of the desired ATG codon by employing the Klenow fragment of DNA polymerase. The plasmid pEVPL also contains a conveniently located BamHI site which may then be cleaved to enable the integration of final aTCGF Segment BE into the linearized pEVPL by ligating (T4 ligase) the blunt end ATG of the plasmid to the blunt end GCA (21-Ala) of the gene segment BE and ligation (T4 ligase) of the complementary cohesive BamHI termini of the respective parts. The resulting transfer vector (pEVPL-aTCGF with its reading direction shown by arrow as shown in FIG. 7) is then used to transform in a conventional manner a suitable bacterial host such as E. Coli which has been modified to carry a lambda lysogen which has a temperature sensitive repressor sequence and which is defective in bacterial lysis, such as E. Coli W3110 lambda Y139. The resulting transformant may be isolated in the conventional manner and a portion tested for expression using cells labelled with $^{35}S$-methionine as described herinafter in Example B. Having obtained a positive indication of expression of desired protein (Example B), the balance of the transformed cells may be subjected to expression by growing the cells for several generations at 30° C., then raising the temperature to 38° C. for 1 hour to effect expression. Assay of sonicated extracts of the cells will reveal TCGF activity but most of the aTCGF produced was found to be insoluble in the cytoplasm. The insoluble active protein may be removed and further concentrated by centrifugation, washing the pellet with aqueous buffer and dissolving in SDS (0.1%). About 50-70%, e.g. 60% of the protein product obtained in this manner is product from expression of the sequence containing the aTCGF sequence. This product may be sequenced using a gas-phase micro-sequentor after fractionation by preparative SDS gel electrophoresis and cutting out and eluting the band corresponding to a protein standard of known and similar molecular weight. In this manner it may be confirmed that a high proportion, e.g. 85-98%, of protein eluted from the gel was product from the expression of the sequence containing the aTCGF sequence. At least a significant portion of such expression product, typically 20-50%, conforms to the 133 amino acid structure of aTCGF beginning wih Ala-Pro-thr- as shown in Table A. The balance, typically 50-80%, represented the incompletely processed precursor of 134 amino acids beginning with Met-Ala-Pro-thr. Expression of the aTCGF coding sequence in bacteria under the influence of the Lambda $P_L$ promoter-operator, especially when employing other control elements provided by the transcription control system of the plasmid pEVPL, including particularly the cII gene ribosome binding site sequence, results in the production of the desired expression product in high quantities. For example, in a small scale (10 liter) fermentor with the strain W3110 lambda Y139 it is indicated that expression product yields may be obtained that are of the order of at least 100 mg./liter of total fermentation mixture, more typically about 200 mg./liter, at a relatively low cell density of 10 dry grams per liter. Since cell densities can be increased such as to the order of 20-30 dry grams per liter, production of the desired expression product may be increased to even higher levels of the order of at least 400-600 mg./liter.

The expression of pEVPL in *E. Coli* W3110 Lambda Y139 is therefore representative of an embodiment of the invention in which the regulator sequence for the repressor protein for the expression vector operator is incorporated within the chromosome of the host bacteria. Procedures for modifying bacteria in this manner are known. For example, the Lambda Y139 lysogen (available NIH Lambda Phage Collection) may be used to prepare phage stock in *E. Coli* C600 by the method described by Maniatis et al., Molecular Cloning, A Laboratory Manual, Cold Spring Harbor Laboratory (1982). The *E. Coli* W3110 is grown in T-broth containing 10 mM $MgSO_4$ and 0.5% maltose to a cell density of $3 \times 10^8$ cells/ml and mixed with phage stock at a multiplicity of infection of 5. The infected cells are allowed to stand at room temperature for 30 minutes, serially diluted into tubes of T-broth and samples from each tube plated on T-plates and incubated at 30° C. until colonies are found. The desired colonies are those able to support growth of wild type Lambda at 42° C. but not at 30° C.

Figure 8:
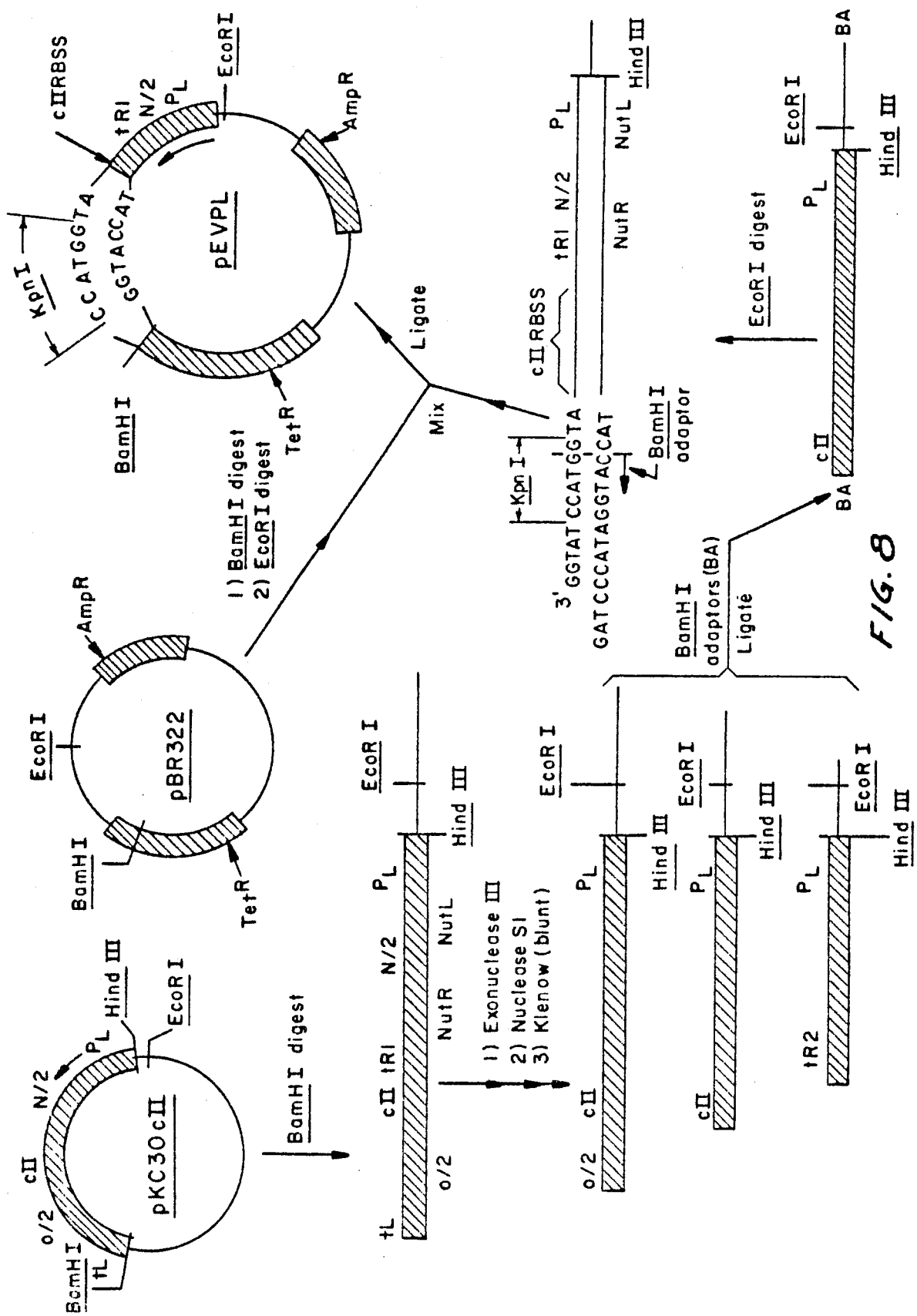
FIG. 8 shows the construction of the plasmid pEVPL.

The plasmid pEVPL and its preparation from a known plasmid is described in detail hereinafter in Example A with reference to FIG. 8.

The aTCGF produced by the invention may be used in a variety of applications as known and indicated in the literature for the other previously known mammalian T-cell growth factor (Taniguchi et al., supra) which has the capacity to support the replication of activated T-cells of mammalian species. These applications include use to promote growth of animal cells in culture and other in vitro applications and also include therapeutic use in treating a variety of conditions. Therapeutic applications of particular interest are based on the recognized immunoregulatory properties of the lymphokine, in particular its use in treatment of conditions due to immunodeficiencies such as the severe combined immunodeficiency syndrome (SCIDS), the acquired immunodeficiency syndrome (AIDS), immunodeficiency states of old age and congental immunodeficiency. However, the aTCGF may also be used as an anti-micotic agent in the treatment of various viral diseases such as cytomegalovirus infections and Herpes virus infections and in the treatment of bacterial infections such as Tuberculosis and Leprosis. Dosages required for such therapeutic use of aTCGF will vary depending upon known factors such as the condition being treated, the severity of the condition and the like. However, satisfactory results may be generally obtained when administered to mammals, e.g. human patients, in daily dosages ranging from 0.1 $\mu$g to 30 $\mu$g/kilogram of body weight. Intravenous administration in a suitable sterile vehicle is generally preferred.

Among the wide variety of particular uses of aTCGF based on its ability to promote T-cell growth in culture are those which find application in diagnostics and in assisting therapeutic treatments. Use in diagnostics is based on the known ability to detect the presence of certain diseases by determining the extent of T-lymphocyte growth in vitro after addition of the lymphokine, using the uptake of radioactive thymidine in the cells as a measure. In assisting therapeutic treatments, such as anti-tumor treatment, the aTCGF may be used to promote in vitro the growth of T-lymphocytes obtained from the patient or other compatible donor, and the resulting proliferated lymphocytes then reinfused to the patient to assist in combatting the condition. In general, the amount of aTCGF to be used to support T-cell growth in culture and other in vitro applications will be similar to the previously known human TCGF in such systems, and may be optimized for particular situations by routine investigations. Mixtures of the (-1)-Met-aTCGF and the mature aTCGF protein may be used in the same manner and at dosages or concentrations similar to those of the mature aTCGF protein based on the indication that the (-1)-Met-aTCGF protein exhibits about the same level of activity as the mature aTCGF protein.

The following examples are representative and designed to illustrate in detail the manner in which certain embodiments of the invention may be practiced. As will be appreciated, work of the type described in the examples is conducted on a very small scale, often involves mixtures, typically relies on the law of probability and fine detection analysis to ascertain successful results and in some cases cannot be exactly duplicated in every fine detail due to, in particular, the natural source or living nature of materials used or produced. Accordingly, it will also be appreciated that reasonably limited repetitions of correct procedures may be occasionally required in reproducing the desired objectives of successful experiments in this field. Temperatures are in °C. unless otherwise noted. In the examples, unless otherwise specified, the TCGF assay used is a thymidine incorporation assay using a mouse cell line (CTLL-2) which is completely dependent on TCGF for growth. In this assay 4000 CTLL-2 cells are seeded in 100 $\mu$l RPMI 1640 with 2% fetal calf serum in 96-well flat-bottom microplates together with 100 $\mu$l of the serially diluted samples to be assayed. After 20 hours at 37° C., cells are pulsed for 4 hours with 0.5 uC of $^3$H-thymidine, collected on glass fiber filter strips using an automatic cell harvester and the incorporated radioactivity determined by liquid scintillation counting.

EXAMPLE 1

Step A: mRNA Preparation From Peripheral Blood Lymphocytes 4 plasmaphersis by-products (purchased from the Red Cross) were fractionated on a Ficoll-Hypaque gradient. The light density cells were collected from the gradient and cultured for 24 hrs in RPMI-164 in the presence of 5% Fetal calf serum, 0.17% Phytohemmaglutinin, and 10 ng/ml phorbal myristate acetate (PMA) at a density of $2 \times 10^6$ cells/ml (a total of $6 \times 10^9$ cells were obtained). The cells were harvested by centrifugation (1000 rpm 5 min.), washed once with phosphate buffered saline (PBS) and finally collected by centrifugation. Cytoplasmic RNA was prepared by a gentle lysis procedure in which the cells were resuspended in 50 ml cold Triton lysis buffer (140 mM NaCl, 1.5 mM M₅Cl₂, 10 mM Tris, pH 8.6, 0.5% Triton X-100) with 10 mM dithiothreitol (DDT) and 50 units/ml RNA sin (purchased from Biotec). This lysate was divided into 2 equal parts and each part was layered over a 10 ml cushion of lysis buffer containing 20% sucrose. The cell nuclei were removed by centrifugation in the cold (4° C., 4000 rpm for 5 minutes). The upper layer (cytoplasmic extract) was carefully removed and sodium dodecylsulfate (SDS) was added to a final concentration of 1%. This solution was extracted 2 times with an equal volume of phenol chloroform (1:1 mixture) and the RNA was precipitated by adding 2.5 volumes of cold ethanol. The precipitated RNA was collected by centrifugation (15 min. at 4000 rpm) and resuspended in 0.01M Tris, pH 7.5, 1 mM EDTA, 0.25M NaCl (TE buffer plus 0.25M NaCl) and reprecipitated by addition of 2.5 vol of cold ethanol. Finally, the RNA was collected by centrifugation and resuspended in 5 ml of H₂O. The final yield was 7.5 mg. Messenger RNA was isolated from the total cytoplasmic RNA by selection on oligo dT cellulose. 2.5 mg of total RNA was heated to 65° for five minutes. NaCl was added to 0.5M and the RNA was allowed to cool to room temperature. This RNA was passed over a one ml column of oligo dT cellulose equilibrated in TE+0.5M NaCl (Binding buffer). Unbound RNA was removed by washing the column extensively with binding buffer. Bound messenger RNA was eluted with 3 ml of H₂O and precipitated by addition of 0.2 ml of 4M NaCl and 2.5 volumes of cold ethanol. The precipitated mRNA was collected by centrifugation (30 minutes at 25,000 rpm). The final pellet (approximately 100 ug) was resuspended in 50 ul H₂O. Confirmation that the final mRNA preparation contained biologically active mTCGF mRNA was accomplished using the standard *Xenopus laevis* oocyte translation system in which 10 fresh oocytes isolated from female African toads (*Xenopus laevis*) were each microinjected with 40 nanoliters of the peripheral blood lymphocyte (PBL) mRNA (1 nanogram per nanoliter). Control oocytes were microinjected with H₂O. The oocytes were incubated for 24 hours at 20° C. in 100 ul Barth's medium (Maniatis et al. Supra p. 351). During this period, each oocyte injected with PBL mRNA should translate, produce and finally secrete mTCGF into the medium while the water injected controls should not. TCGF activity was determined using a standard assay protocol, and it was found that the Xenopus oocyte injected with PBL mRNA synthesized significant levels of TCGF activity while the water-injected controls did not.

Step B: First Strand cDNA Reaction 20 ug of PBL mRNA in 10 ul of H₂O was treated with 0.1M methyl mercury for 10 minutes at room temperature. The menthyl mercury was inactivated by addition of 10 ul of 100 mM B-mercaptoethanol. This denatured mRNA was diluted into a 100 ul cDNA synthesis reaction containing 100 mM Tris pH 8.4, 140 mM KCl, 10 mM MgCl₂, 10 mM B-mercaptoethanol, 500 uM each of dATP, dGTP, dCTP and dTTP, 5 ug. of oligo-dT (average length 12-18) as primer, 75 uCi of ³²PdCTP (400 Ci/mmole) and 20 units of the ribonuclease inhibitor RNA sin. The reaction was initiated by addition of 40 units of reverse transcriptase at 37° C. and incubated for 30 minutes at 42° C. The reaction was stopped by addition of EDTA to 40 mM and NaOH to 0.1M at 68° C. for 10 min. The base was neutralized by addition of Tris.HCl, pH 7.5 to 0.1M and an equivalent amount of HCl. The reaction mix was next entracted by an equal volume of water saturated phenol:chloroform (50:50 mix). The phenol phase was back extracted with 50 ul of TE buffer. The aqueous phases were pooled and the single-stranded cDNA was isolated by passing the mixture over a 5 ml Sepharose CL-4B column equilibrated with 10 mM Tris, 1 mM EDTA, pH 8.0. The excluded fractions were brought to 250 mM NaCl and the cDNA precipitated by adding 2.5 volumes of cold ethanol. The cDNA was collected by centrifugation for 30 min at 25,000 RPM. The final pellet (2 ug of cDNA) was resuspended in 50 ul of H₂O.

Step C: Second Strand Reaction

Second strand cDNA was synthesized using the Klenow fragment of DNA polymerase I. The reaction mix (200 ul) contained 2 ug of cDNA, 50 mM potassium phosphate, pH 7.4, 10 mM MgCl₂, 250 uM of all four deoxynucleoside triphosphates, 10 mM 2-mercaptoethanol and 6 units of the Klenow enzyme. The mix was incubated at 37° for 1 hr. The reaction was stopped by the addition of EDTA to 50 mM and extracted with an equal volume of phenol:chloroform. The aqueous phase was passed over a 5 ul sepharose CL-4B column to remove the phosphate buffer. The excluded fraction was concentrated by ethanol precipitation as described above (Step B).

Step D: S1-nuclease digestion

The loopback cDNA was converted to a clonable form by cleaving the loop with nuclease S1. To do this 0.75 ug of double strand cDNA in a 300 ul reaction containing sodium acetate pH 4.5, 1 mM Zn Acetate and 0.1 NaCl was incubated for 30 minutes at 30° with 12 units of S1. The reaction was terminated by extraction with an equal volume of phenol. The phenol phase was back extracted with 50 ul of TE and the pooled aqueous phases were passed over a 5 ml Sepharose Cl-4B column as described above. Fractions of 150 ul were collected and the first three, (the excluded cDNA fractions) were pooled and the nucleic acids precipitated by addition of NaCl to 0.25M and 2.5 volumes of cold ethanol. The cDNA was collected by centrifugation (30 min. at 25,000 rpm) and resuspended in 40 ul of H₂O. The final yield was 340 ng of cDNA.

Step E: Recombinant cDNA Preparation

Homopolymeric C "tails" were added to the ends of the cDNA by gently heating 100 ng of cDNA in a 50 ul reaction mixture containing 0.1M B-mercaptoethanol 1 mM CoCl₂ and 6 units of terminal deoxynucleotidyl tranferase at 37° C. for 5 minutes. The reaction was terminated by the addition of EDTA to 40 mM and heating to 68° C. for 10 minutes. 50 ng of this tailed cDNA was annealed with 250 ng of G-tailed pBR322 which had been linearized by digestion with the restriction endonuclease Pst 1 (and tailed with dGTP as described above for the C-tailing of the cDNA) in 50 ul of 10 mM Tris, pH 7.5, 1 mM EDTA, and 100 mM NaCl. The annealing reaction was performed at 50° C. for 2 hours after a 5 minute preincubation at 68° C. Steps B-E above are represented in FIG. 1.

Step F: Bacterial transformation

The cDNA annealing reaction product was used directly to transform the *E. coli* strain MC1061. A fresh colony of bacterial cells were used to inoculate 50 ml of L-broth and grown for several hours until the optical density at 550 nm was 0.25. The cells were chilled on ice and harvested by centrifugation (4000 rpm for 10 min.). The pellet was resuspended in 10 ml of cold 0.1M CaCl$_2$ and allowed to sit on ice for 10 min. The cells were collected by centrifugation (4000 rpm for 5 minutes) and resuspended in 2.5 ml of 0.1M CaCl$_2$. 20 ul of the cDNA annealing reaction was then incubated with 400 ul of CaCl$_2$-treated bacteria for 30 minutes on ice and then for 2 minutes at 37° C., followed by addition of 1.6 ml of L-broth and final incubation for 30 minutes at 37° C. Ten of these transformations were performed utilizing all of the annealed cDNA. Each transformation mixture was spread directly onto nitrocellulose filters placed on the surface of standard 1% Agar L-broth plates (10 cm diameter) containing 10 ug per ml tetracycline. From the ten transformations, a total of 100 such plates were spead and incubated overnight at 37° C. On the average approximately 400 bacterial colonies grew on each plate for a total of 40,000 clones.

Step G: Replica Plating

Two identical replicas were prepared from each filter (Step F, above) by standard replica plating methods, in which each filter from the original library (the master filter) was carefully removed from its agar dish and placed colony side up on a sterile square of filter paper (Whatman 3 MM) resting on a square piece of glass. A new, pre-wetted nitrocellulose filter was carefully aligned on top of the master filter, covered with a second sterile square of filter paper and the complete sandwich then pressed together firmly with a second piece of glass. The sandwiched filters were numbered and 3 pinholes were punched through them asymmetrically so that they could be exactly aligned again in the future. The replica was then removed from the master and placed colony side up on a new tetracycline-containing L-broth agar plate. A second replica was immediately prepared in identical fashion. Each master filter was returned to its respective petri dish and all of the plates were incubated at 37° for several hours until the bacterial colonies had reached approximately 1 mm in diameter. At this time, all of the replica filters were transferred to fresh agar plates containing L-broth plus 10 ug per ml tetracycline and 150 ug per ml chloramphenicol. These plates were incubated overnight at 37° C. to allow the plasmid in each to amplify. The original masterplates were stored at 4° C.

Step H: Preparation of filters for hybridization

Each replica filter (Step G) was placed (colony side up) on filter papers (Whatman 3 mm) soaked in 0.5M NaOH, 1.5M NaCl for seven minutes. The filters were transferred to neutralization filter papers (soaked in 1M Tris, pH 7.5, 1.5M NaCl) for 2 minutes and then transferred to a second set of neutralization filters for 5-10 minutes. Finally, the filters were placed on filters soaked in SSC buffer (0.015M Sodium Citrate, 0.15M NaCl, pH 7.4) for 5 minutes, air-dried and baked in vacuo at 80° C. for 1-2 hours.

Step I: Hybridization Probe Preparation

Two independent 17 nucleotide probes were chemically synthesized employing the known solid phase phosphite triester method. The first probe intended as a 5' probe conformed to the structure d(G-C-A-C-C-T-A-C-T-T-C-A-A-G-T-T-C) and the second probe (a 3' probe) conformed to the structure d(C-T-G-A-T-T-A-A-G-T-C-C-C-T-G-G-G). Each such 17 oligonucleotide probe was labeled at its 5' end using $\gamma^{32}$P-ATP and polynucleotide kinase by forming a reaction mixture (25 ul) contained 10 pM of oligonucleotide, 10 pM $\gamma$ $^{32}$P-ATP (300 Ci/mmole) 50 mM Tris, pH 7.6, 10 mM MgCl$_2$, 5 mM DTT and 10 units of T4 polynucleotide kinase. The reaction mixture was incubated at 37° C. for 30 minutes and stopped by the addition of TE+0.1M NaCl to 100 ul and an equal volume of phenol:CHCl$_3$ (1-1 mix). The aqueous layer was passed over a 5 ml Sephacryl S-200 (purchased from Pharmacia) column equilibrated in TE to remove unincorporated label.

Step J: Screening the cDNA library filters

Each set of duplicate filters was incubated at 68° C. for 1 hour in pre-hybridization mix (4×SSC, 100 ug/ml Herring sperm DNA, 5× Denhardt's solution, (0.2% Ficoll purchased from Sigma, 0.2% polyvinyl-pyrrolidone, 0.2% Bovine Serum Albumin) and 0.1% SDS). After the prehybridization, bacterial debris were removed from each filter by wiping with a tissue. One set of filters was annealed with the 5' specific $^{32}$P-labeled probe while the other set was annealed with the 3' specific probe. The annealing reactions were performed in the prehybridization mix (as above) with the addition of 100,000 cpm per ml of labeled probe. Each set of filters was incubated in these reactions overnight at 30° C. with gentle shaking. The filters were then washed with several changes of 4×SSC+0.1% SDS at room temperature for 1 hour and then exposed to X-ray film for 6-12 hours at −70° C. with intensifying screens. By lining up the X-ray film exposures of the duplicate filters, it was seen that a number of colonies hybridized to one or the other hybridization probe but only six colonies hybridized with both probes (out of approximately 40,000 colonies). The films of these filters were aligned with the original master filter containing the live bacterial colonies from this alignment. Each clone which hybridized with both probes was picked from the master filters and grown overnight in 2 ml of L-broth plus 20 ug/ml tetracycline.

Step K: Analysis of the clones

Plasmid DNA was prepared from each of six small overnight cultures using a standard rapid DNA preparation method. To do this, the bacterial cells were harvested by centrifugation (2 minutes in the microfuge) and resuspended in 100 ul of 50 mM glucose, 25 mM Tris, pH 7.5, 1 mM EDTA containing 0.25 mg lysozyme at 0° for 30 minutes. Next, the bacteria were disrupted by the addition of 200 ul 0.2M NaOH, 1% SDS at 0° for 5 minutes. The lysate was neutralized by addition of 150 ul of 3M sodium acetate, pH 4.8 and allowed to sit on ice for 15 minutes. The precipitate of denatured protein and chromosomal DNA was removed by centrifugation (10 minutes in the microfuge at 4° C.). The supernatent was extracted once with phenol/chloroform (1:1 mix) and the nucleic acids precipitated by the addition of 2.5 volumes of cold ethanol. The nucleic acids were collected by centrifugation (10 minutes in the microfuge) resuspended in 250 ul of 0.1M sodium acetate, 50 mM Tris pH 8 and reprecipitated by the addition of 2.5 volumes of cold ethanol. The final plasmid DNA was resuspended in 50 ul of TE and a portion used to form a reaction mixture (15 ul) containing 0.05M Tris, pH 8, 10 mM MgCl$_2$, 50 mM NaCl, 7 ul of the plasmid DNA and 2 units of the restriction endonuclease Pst1. After 1 hour at 37° C., bromophenol blue (tracking dye) was added to 0.005% and each reaction mix was electrophoresed on a small TBE (50 mM Tris-Borate, pH 8.3, 1 mM EDTA) agarose gel containing 1 ug/ml Ethidium bromide for 2 hours at 100 volts. The DNA fragments were visualized by illuminating the gel with ultraviolet light and the results recorded by taking a polaroid photograph of the irradiated gel. Because the cDNA clones were constructed by inserting C-tailed cDNA's into a G-tailed pBR322 vector (linearized at the Pst 1 site), digestion of each plasmid with Pst 1 should excise the insert from the plasmid vector allowing a determination of the cDNA insert size. Agarose gel electrophoresis of the six Pst1 cut plasmids revealed five of the six clones had inserts of approximately 800 base pairs while the sixth clone had an 1100 nucleotide insert. To confirm that each of these six clones were the same as those identified by colony hybridization, the DNA from the Pst 1 digestions were analyzed by the Southern Blot hybridization procedure to the original 17-mer oligonucleotide probes. In such procedure the agarose gel was treated with 0.5M NaOH, 1.5M NaCl for 30 minutes at room temperature to denature the DNA in the gel. The gel was neutralized by gently shaking it in excess 1M Tris, pH 7.5, 1.5M NaCl. Two nitrocellulose filters were cut to the size of the gel, wetted with 2×SSC, and carefully placed on both sides of the gel. The gel, sandwiched between the 2 filters, was placed on top of a stack of paper towels (about 2 cm high) and covered with another layer of paper towels (also about 2 cm). Finally, the whole assembly was covered with a small glass square which was weighted in place with about 500 grams and allowed to stand overnight. By this method, liquid leached out of the gel in both directions into the paper towels. DNA present in the gel also transfers out of the gel but is retained on the nitrocellulose filters. The filters were then used in hybridization experiments in which the filters are air dried, baked in vacuo (80° C. for 1 hour), incubated in pre-hybridization mix (Step J, above) at 68° C., for 1 hour and each filter then hybridized with one or the other of the original chemically synthesized probes (prehybridization mix plus $10^6$ cpm/ml $^{32}$P-labeled oligonucleotide; 30° C. for 2 hours). After hybridization, the filters were rinsed for 30 minutes with 4×SSC+0.1% SDS and exposed to X-ray film. Each of the six Pst1 inserts hybridized with both probes.

Step L:

In sequencing four of the six cDNA clone, one clone was identified which had an amino acid sequence which was distinct from that of the currently known sequence for T-Cell Growth Factor. The sequencing of the insert of this clone (pBR322-aTCGF) was carried out in accord with two procedures involving a) dideoxy DNA sequence and b) Maxam Gilbert sequencing, as follows:
a) by dideoxy DNA sequencing, the general details and procedures thereof being described in the M13 Cloning Dideoxy Sequencing Manual published by Bethesda Research Laboratories, Inc., Bethesda, Md (1980). Inserts for subcloning into M13 vectors were prepared by both of the methods: (a-1) nucleotide deletion (degradation); and (a-2) restriction endonuclease cleavage. Additional dideoxy sequencing was performed on denatured super coiled pBR322-aTCGF as discussed in a-3 below.

Figure 2:
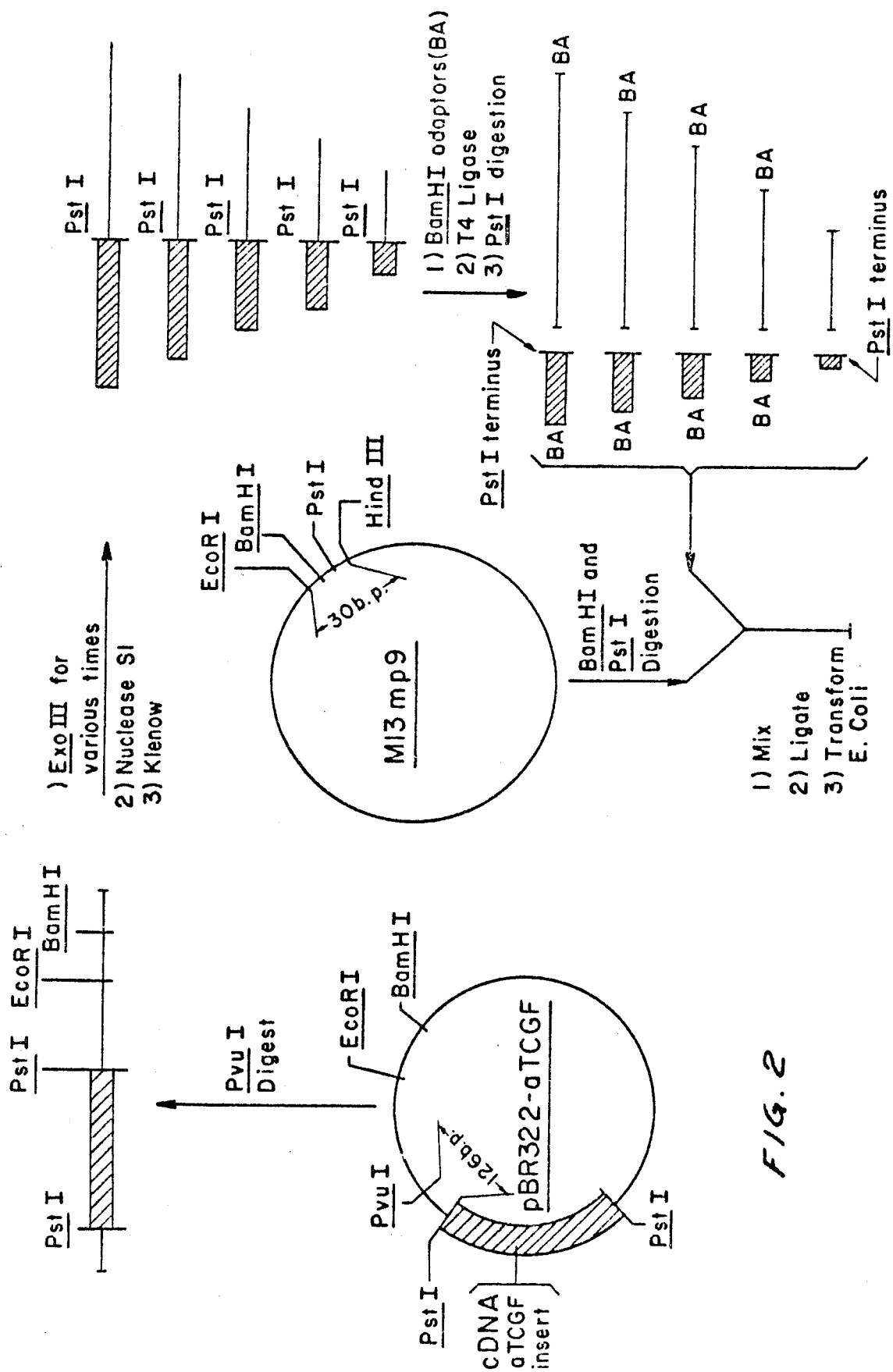

In method (a-1) as shown in FIG. 2, the cloned DNA (pBR322-aTCGF) was cleaved with Pvu I (i.e. 126 nucleotides from the Pst I site where the cDNA insert was integrated into pBR322), and 5 ug of the Pvu I linearized DNA was incubated at 30° with 600 units of Exonuclease III (to degrade each strand of the duplex DNA sequentially from its 3' ends) in 100 ul of 50 mM Tris, pH 8 10 mM 2-mercaptoethanol and 5 mM MgCl$_2$. Then 14 ul samples of the reaction were removed after 1 min, 2 min., 3 min., 4 min. and 5 min. and added to a tube containing 300 ul of ExoIII quench (20 mM EDTA, 0.5M NaCl). The degraded and ethanol precipitated DNA was then incubated in 160 ul of 30 mM Na Acetate, pH 4.6, 200 mM NaCl, 1 mM ZnSO$_4$ and 40 units of S1 nuclease. The reaction was stopped after about 30 minutes at 30° by the addition of 40 ul of 0.5M Tris-HCl, pH 8.0, 1M NaCl. The ethanol precipitated and collected DNA was then incubated in 100 ul of 10 mM Tris-HCl pH 7.5, 100 uM each of dATP, dCTP, dGTP and dTTP, 1 mM DTT, 10 mM MgCl$_2$ and 5 units of Klenow Fragment of DNA polymerase I for 15 min. at 37°. The reaction was stopped by addition of NaCl (4M) to final 0.2M concentration and extraction with phenol/chloroform. The resulting blunt ended DNA segments of varying length (represented by the five segments in FIG. 2) were collected by ethanol precipitation and ligated to BamHI adaptors prepared by treating 300 pmole of the 11-mer with T4 polynucleotide kinase and 1 mM ATP, stopping the reaction by extraction with phenol/chloroform and chloroform, adding 300 pmole of the 15-mer, and ethanol precipitating. The 15-mer plus 11-mer were resuspended in 30 ul of 10 mM Tris, pH 7.5, 1 mM EDTA, 0.2M NaCl and annealed at 15° for 2 hours. The adaptor structure is as follows:

The adaptor (15 pmole) was then incubated with the degraded and blunted DNA in 30 ul of 15 mM Tris-Hcl pH 7.5, 10 mM MgCl$_2$, 10 mM DTT, 100 uM ATP and 0.1 unit of T4 ligase at 15° for 90 minutes. The reaction was stopped by heating at 68° for 15 min. The "Bam-adapted" DNA was then digested with the Pst I (20 units) for 4 hours at 37° after adding NaCl to 66 mM (final volume 31 ul). To isolate fragments of the appropriate size, the Pst I digestion reaction was fractionated by electrophoresis through a 1% tris-acetate (0.04M Tris-acetate, pH 8.3, 0.001M EDTA) agarose gel in the presence of ethidium bromide. Five size classes of the deleted DNA were isolated by carefully cutting and isolating five separate regions of the gel between 200 and 800 nucleotides using the glass powder isolation protocol, see below. As illustrated in FIG. 2, the bacteriophage M13 vector mp9 (100 ug) was prepared by digesting with 150 units of BamHI and 150 units Pst I. The linearized mp9 vector DNA was separated from the resulting small oligonucleotide fragment by passing the reaction mix (100 ul) over a 2 ml gel filtration column (Sepharose CL-4B) equilibrated in 10 mM Tris-HCl pH 7.5, and 1 mM EDTA (TE). The excluded fractions were pooled, brought to 0.4M NaCl, precipitated with ethanol, resuspended in 100 ul of TE and the linearized M13mp9 vector preparation diluted 25 fold (to 40 ng/ul). As indicated in FIG. 2, each (5 ul) of the 5 pools of degraded cDNA fragments was ligated to the linearized M13mp9 vector (20 ng) in a 20 ul ligation mix. After 90 min at 15° the reaction was terminated by heating at 68° for 15 minutes. E. coli strain JM101 (45 ml) which had been exponentially growing in SOBM medium (20 g tryptone, 5 g yeast extract, 0.58 g NaCl and 0.11 g KOH, 10 mmole MgSO$_4$ per liter) were collected by centrifugation, (10 min. at 2500 rpm at 4° C.). The pellet were resuspended in 3.1 ml of cold Tfb (100 mM RbCl, 45 mM MgCl$_2$, 50 mM CaCl$_2$, 10 mM Potassium MES (2-[N-Morpholine]ethanesulfonate)) and incubated at 0° for 10 minutes as indicated in FIG. 2. Each (2 ul) of the ligation reaction mixes was then incubated in 200 ul of the calcium treated bacteria for 30 min. at 0°. The transformation mix was heated briefly (90 seconds) to 42° and 4 ml aliquots of melted top agar (Luria Broth+0.9% Agar) containing 100 ul of a saturated culture of JM101, 10 ul of 0.1M IPTG (isopropylthiogalactoside) and 100 ul of 2% X-gal (5-bromo-4-chloro-3-indolyl-beta-D-galactoside) were added and the mixture spread over the surface of 0.9% Agar plate containing Luria Broth. The plates were incubated overnight at 37° to allow phage plaques to develop. Because the M13 vector carries the *E. coli* beta-galactosidase gene, all plaques from nonrecombinant phages will be blue because of the IPTG and X-gal included in the plating mix (a plaque is a clearing in the lawn of bacteria on the plate caused by a bacteriophage clone). If, however, the beta-galactosidase gene is interrupted by insertion of a piece of foreign DNA, then beta-galactosidase will not be expressed and the phage plaques will be colorless (or white). Each transformation yielded between 20 and 130 white plaques. To identify the desired phage clones carrying TCGF DNA sequences, an imprint of each plate was prepared by carefully placing an 85 mm circular nitrocellulose filter on the agar surface. The filter was carefully lifted from the plate after marking it orientation relative to the surface of the plate. This filter, which picked up small amounts of phage particles at the location of each plaque, was rinsed briefly in 0.5M Tris, pH 7.5, 1.5M NaCl, then in 1×SSC and finally was baked in vacuo at 80° for 2 hours. The filter was hybridized to the aTCGF cDNA insert (labeled with $^{32}$P by nick-translation Rigby, et al *J. Mol. Biol.* 113: 237) using the standard hybridization procedure with incubation at 68°. Two plaques that hybridized to the labeled probe were picked from each of the original size classes of degraded cDNA fragments for sequencing. Each positive plaque was picked with a pasteur pipet and transferred into 2 ml of JM101 which had been freshly diluted 100 fold with SOBM broth. Each infected culture was grown at 37° for 4.5–6 hours with vigorous shaking. The bacteria were then removed from each culture by centrifugation (5 min. in the microfuge). The phage-containing supernatants were collected, 150 ul of 20% polyethylene glycol and 2.5M NaCl was added and the phage allowed to precipitate for 10 min. at room Temp. Each precipitate was collected (5 min. in microfuge) being careful to remove all of the supernatant. The pellets were each resuspended in 100 ul of TE, 0.3M sodium acetate, extracted with phenol and the DNA was ethanol precipitated from the aqueous phase. Each DNA pellet was rinsed with 95% ethanol, dried in vacuo and resuspended in 30 ul of TE buffer. DNA sequence was obtained from four of the resulting collection of single stranded templates is shown in FIG. 3 with the solid line portion representing the stretch actually sequenced and the dotted line portions not sequenced.

In method (a-2)-restriction cleavage-templates for dideoxy sequencing were generated by cleavage of 10 ug of the pBR322-aTCGF with combinations of restriction enzymes (indicated in FIG. 3), gel purifying the fragments and ligating them to the appropriate M13 vectors as described above for the deletion series (method a-1). These fragments included the 230 base pair RsaI to XbaI fragment at the 5' end of the sequence cloned between the SmaI and XbaI sites of mp10 and mp11 (to obtain both orientations) and the 520 base pair fragment generated by cleavage with XbaI and PstI at the 3' end of the sequence cloned between the XbaI and PstI sites of Mp11. The sequences obtained from these clones is indicated in FIG. 3.

(a-3) Additional dideoxy sequence was obtained using rapid prep pBR322-aTCGF DNA using the 5' 17mer as primer. To do this, a 5 ul overnight culture of pBR322-aTCGF was harvested by centrifugation (8,000 RPM, Sorvall 5534 rotor 5 min.) and treated with lysozyme (100 ul of 50 mM Tris-HCl, pH 8.0, 50 mM glucose, 10 mM EDTA and ·2.5 mg/ml lysozyme for 10 min at room temperature). The cells were lysed by addition of 200 ul of 1% SDS in 0.2M NaOH. The resulting solution was neutralized by addition of 150 ul of 5M Sodium acetate pH 4.8. After sitting on ice for 10 min, the tube was spun in the microfuge (eppindorf) for 10 min at 1° cC. The supernatant was removed and extracted one time with phenol. The aqueous phase was removed and precipitated by the addition of 800 ul of 95% ethanol at room temperature. The DNA was collected by centrifugation (5 min in the microfuge) and the pellet rinsed with 500 ul of 70% ethanol to remove traces of phenol. The DNA was resuspended in 400 ul of 50 mM Tris.HCl, pH 7.5, 0.1 mM EDTA containing RNase (20 ug/ml) and incubated for 20 min at room temp. to degrade contaminating RNA. This reaction was extracted one time with phenol and ethanol precipitated three times and the final pellet rinsed with 70% ethanol before resuspending in 20 ul of water. Half of this DNA (about 2 ug) was used in the sequencing reaction. To perform dideoxysequencing on this double stranded DNA, the DNA (10 ul) was mixed with 2 ul of 2M NaOH, 2 mM EDTA and 8 ul of water to denature the strands. This mix was neutralized by the addition of 10 ul of 4M NH$_4$OAc, pH 4.5 and 100 ul of ethanol and the mix was quick-chilled in a dry ice ethanol bath. The denatured DNA was collected by a 3 min spin (eppendorf). The pellet was dried and resuspended in 8 ul of H$_2$O. This DNA was sequenced using the standard M13 dideoxy reactions with 5 pmole of the 5' 17mer as primer. The sequence obtained from this protocol is indicated in FIG. 3.

(b) Standard Maxam-Gilbert sequencing was used to obtain the sequences at either end of the clone. As represented in FIG. 4, the pBR322-aTCGF was digested with PstI and the ends of the aTCGF insert were labeled using terminal transferase and $^{32}$P-cordysepin (Tu, C.-P. D. and Cohen, S. N. *Gene* 10: 177–183 (1980)). This DNA was cut with XbaI and the resulting fragments were resolved from one another by electrophoresis through a 1.0% Agarose gel, and isolated from the gel by the glass powder protocol. In this protocol, the desired fragments are excised from the ultra violet illuminated agarose gel. The agarose slices are dissolved in NaI solution (90% NaI, 1.5% Na$_2$SO$_3$) using 1 ml of solution per gram of gel slice. The DNA is next absorbed to 5 ul of a 50% slurry of acid washed glass powder (325 mesh silica) (5 ul will bind up to 20 ug of DNA) for 15 min. on ice. The glass powder is collected by centrifugation (1 min. in the microfuge) and washed 2 times with 100 ul of NaI solution. To remove traces of NaI, the glass powder pellet is washed 2 times with cold 50% ethanol containing 0.1M NaCl, 10 mM Tris-HCl, pH 7.5, 1 mM EDTA. Finally, the DNA is eluted from the glass by incubation at 37° with 10 ul of 10 mM Tris-HCl, pH 7.5 1 mM EDTA. The fragments were then sequenced by the standard chemical degradation method, and the length sequenced is shown in FIG. 4 by solid lines.

The results of all of the sequencing of the insert from pBR322-aTCGF in terms of the sequence elucidated thereby are given in Table A, above. The *E. coli* MC1061 isolate transformed with pBR322-aTCGF was also internally designated *E. coli* MC1061-pTCGF-11 and such designation was used in depositing the same with the ATCC, as above-indicated (Accession No. 39673).

Step M: Transfer Vector for Expression in Animal Cells

Twenty-five micrograms of pBR322-aTCGF and twenty-five micrograms of pCVSVL were separately digested with 25 units of Pst1 (100 ul of 0.01M Tris, pH 7.5, 10 mM MgCl$_2$, 25 mM NaCl). Each reaction mix was heated inactivated and loaded directly onto a 1% agarose gel after addition of SDS to 0.1% and bromophenol blue to 0.001%. After electrophoresing the bromophenol blue dye to the bottom of the gel, the DNA was visualized by illumination with a long wavelength ultra violet light and the linearized pCVSVL fragment and the aTCGF insert fragment were cut from the gel and purified by binding to powdered glass (see Step L). 25 ng of the vector were ligated to 5 ng of the liberated aTCGF insert in 10 ul of 10 mM Tris, pH 7.5, 10 mM MgCl$_2$, 1 MM ATP, 1 mM DTT and 0.2 units of T4 ligase for 2 hours at 16° C. Half of this reaction was used to transform 200 ul of competent *E. coli* MC1061 (as described in Step F). The transformation was spread onto 5 L plus tet plates. Replica filters were prepared and hybridized with the 5' 17 mer. Six colonies which hybridized with the labeled 17 mer were picked and grown for further analysis.

Figure 5:
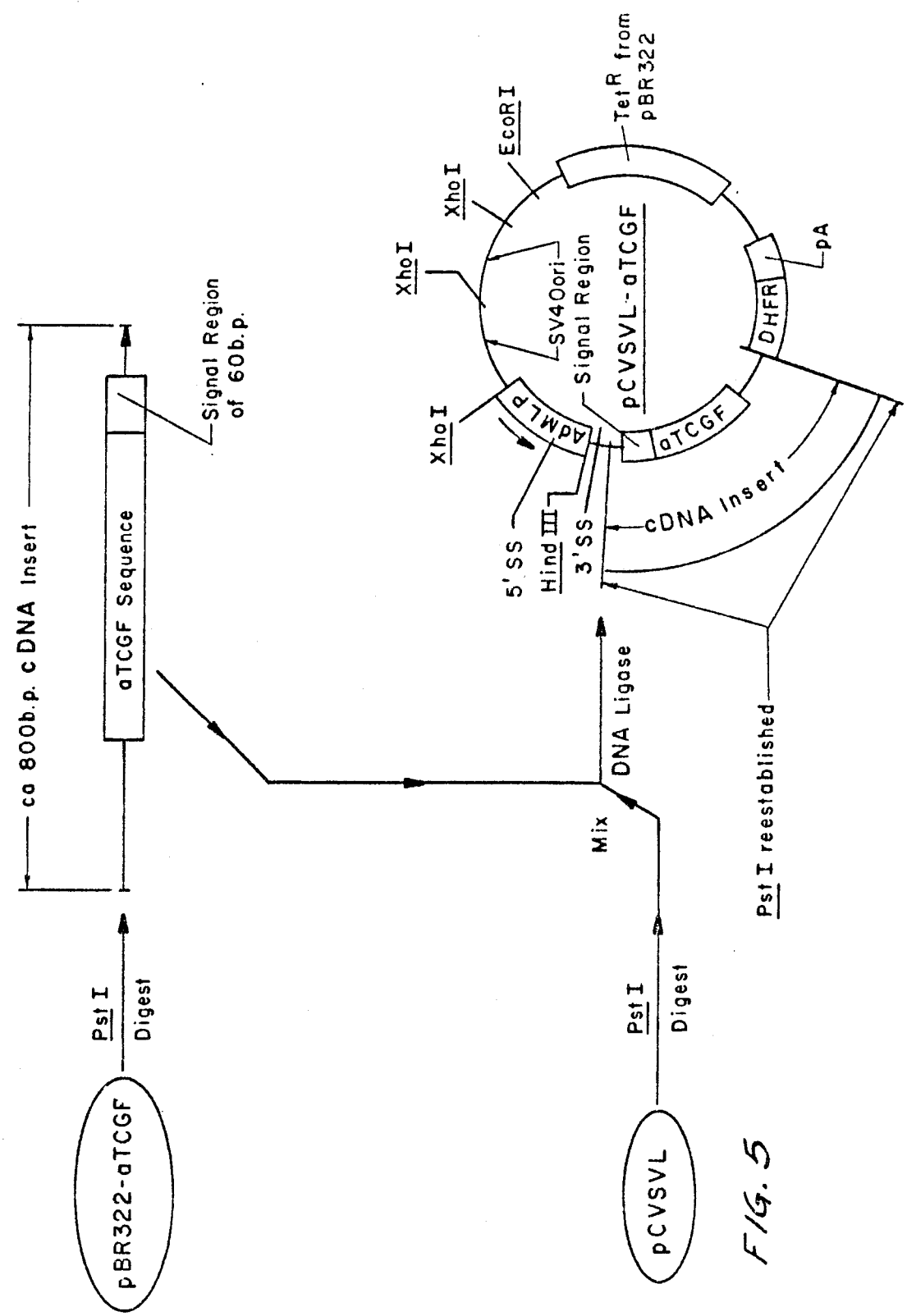
FIG. 5 shows the construction from the pBR322-aTCGF discovered by the sequencing of a transfer vector pCVSVL-aTCGF for purposes of producing aTCGF in animal cells.

Rapid prep DNA was mapped using the restriction enzymes XbaI and XhoI to determine the orientation of the insert relative to the adeno major late promoter in the vector segment. Clones carrying the aTCGF insert in either orientation were identified (See FIG. 5). DNA from 1-liter cultures of these clones were prepared by equilibrium density centrifugation as follows:

1. Grow 1 liter of plasmid containing bacteria overnight in L-broth (10–15 ug/ml Tet).
2. Harvest cells (−4000 rpm in Beckman R-6B, 10 minutes).
3. Wash cells in 250 ml cold TE (10 mM Tris-HCl, 1 mM EDTA, ph 8).
4. Resuspend cells in 15–20 ml of 25% sucrose, (0.05M Tris-HCl, pH 7.5 at 0° C.)
5. Add 1/10 volume (1.5–2.0 ml) of lysozyme (10 mg/ml in sucrose solution). Incubate on ice 10 min.
6. Add 1/5 volume (3–4 ml) 0.5M EDTA, pH 8. Incubate on ice for 5 min.
7. Dilute suspension 1:1 with cold Triton lysis solution (0.1% Triton X-100, 60 mM EDTA, 50 mM Tris-HCl, pH 8). Incubate on ice 10 min.
8. Spin 18K in Sorval SS34 rotor for 30 minutes.
9. Decant the supernatant. Add 0.95 g/ml CsCl and 1/10 volume 10 mg/ml ethidium bromide. The refractive index should be between 1.390 and 1.396.
10. Spin at 45K in the 50.2 Ti (Beckman) rotor for 2 days.
11. Using a longwave UV light to illuminate the tube, carefully withdraw the plasmid DNA (lower band) from the gradient. Remove the ethidium bromide from the DNA by extracting with an equal volume of TE saturated butanol three times. Finally, precipitate the DNA by diluting it 1:3 with water and adding 2.5 volumes of ethanol (−20° C. for 3–4 hours). Collect the precipitate by centrifugation (4000 RPM, Beckman R6B, 15 min). Resuspend in 200 ul H$_2$O.

Step N: Expression of pCVSVL-aTCGF in Animal Cells

Following the DEAE-Dextran method described by Sompayrac et al., Proc. Nat. Acad. Sci. USA 78, 7578—7578 (1981), 10 cm dishes of subconfluent COS-7 monkey cells were transfected with 8 ug of DNA from the correct orientation pCVSVL-aTCGF construct; from the opposite orientation clone; or from DNA from pCVSVL alone. Each transfection was performed using 4 ml of DEAE-Dextran solution for 10 hours. After rinsing with DME (purchased from Gibco), the cells were treated with DME containing 0.1 mM choroquin, as more particularly described by Luthman et al., Nuc. Acids Res. 11, 1295–1308 (1983). After 2.5 hr at 37°, this medium was replaced with DME+10% heat inactivated fetal calf serum and the dishes were incubated for 48 hours. The conditioned medium (8 ml) was collected and the cells were scraped into 5 ml of cold phosphate buffered saline. The cells were then collected by centrifugation (15 minutes in the Beckman model 6B) and the conditioned medium was assayed using the TCGF dependent mouse cell line CTLL-2 (described by Stull et al., J. Immunol. 126, 1680–1683 (1981)). In this assay, $10^4$ CTLL-2 cells are incubated for 24 hours in microtiter wells in 2-fold serial dilutions of the sample to be assayed. The mouse cells are then pulse labelled for 4 hours with 0.5 uC/well H$^3$Thymidine. The cells were collected on glass fiber paper using an automatic harvesting device and the radioactivity in the cells determined. One unit of TCGF activity/ml is defined as the dilution of a laboratory standard which gives 50% of maximal incorporation using $10^4$ cells in 200 ul of RPMI-1640 plus 2% FCA. By this assay it was found that only the transfection of monkey COS-7 cells with the transfer vector pCVSVL-aTCGF carrying the insert in the correct orientation resulted in the production of measurable TCGF activity. In this transient system, 5–10 units of aTCGF were produced per ml. Isolation of the active expression product from monkey COS-7 cell medium and sequencing of this protein confirms that aTCGF conforms to the structure of polypeptide having sequentially the amino acids 21-153, inclusive, as set forth in Table A, above, with normal N- and free acid C-termini.

EXAMPLE 2

EXPRESSION OF aTCGF IN BACTERIA AND TRANSFER VECTOR THEREFOR

Step A: Preparation of Blunt Ended aTCGF Segment BE for Integration Into pEVPL

The strategy for expression of aTCGF in the plasmid pEVPL involved, as shown FIGS. 6 and 7, the preparation (as shown in FIG. 6) of a blunt ended aTCGF segment (BE) in which the signal peptide region elucidated in the natural structure is exactly removed. To do this, the aTCGF insert was first subcloned into a bacteriophage M13 vector in order to obtain a single-stranded form of the coding region for more convenient manipulations. As shown in FIG. 6, M13 mp9 (30 ug of DNA) was cleaved with 50 units of Pst I in 50 ul of 25 mM Tris-HCl, pH 7.5, 10 mM mgCl₂, 25 mM NaCl for 1 hr at 37°) and the pBR322-aTCGF DNA was also cleaved with the same enzyme (same digestion conditions). After phenol extraction and ethanol precipitation the two PstI cleaved DNAs were ligated (100 ng of M13 mp9 DNA and 200 ng of pBR322-aTCGF in 10 ul of 50 mM Tris, pH 7.5, 10 mM MgCl₂ 1 mM ATP, 1 mM dithiothreitol and 0.5 units of T4 ligase for 2 hours at 16° C.) together to form dsM13-aTCGF which is then used to transform E. coli strain JM101. Individual plaques were tested for the presence of aTCGF sequences in the correct orientation by hybridization to the 5' 17 mer that was used originally to identify the mTCGF clones (GCACCTACTTCAAGTTC). One such plaque was picked and used to infect a 100 ml culture of JM101. After 12 hours, the recombinant phage (ssM13-aTCGF) was isolated from this phage preparation for use in further manipulations. The 5" 17 mer with its 5' end being the first nucleotide of the first-codon of mature aTCGF (ala-21), was used as a primer for beginning synthesis of a second strand on the single-stranded template ssM13-aTCGF. The synthesis begins precisely at the desired spot (that is the codon for ala-21). By copying the coding region beginning at this primer site and then digesting all of the single-stranded regions with S1-nuclease, a population of linear DNA molecules can be generated, each beginning with a blunt end (at the codon for ala-21) and terminating at random in the M13mp9 vector segment beyond the aTCGF coding region. The primary reaction was accomplished by mixing 25 ug of ssM13-aTCGF with 20 pM of the 17 mer (21-ala primer) in 25 ul of 10 mM Tris, pH 7.5, 1 mM EDTA, 50 mM NaCl, 5 mM 2-mercaptoethanol, 100 uM of each dGTP, dCTP, dATP, and dTTP and 8 units of the Klenow fragment of DNA polymerase for 30 minutes at room temperature. The reaction was stopped by incubation at 65° for 10 minutes, then diluted to 100 ul with S1 buffer (30 mM sodium acetate, pH 4.6, 200 mM NaCl and 1 mM Zn SO₄) and incubated for 30 minutes at 30° with 25 units of Nuclease S1. The resulting linear DNA is then treated in 0.1 ml of 10 mM Tris, pH 7.5, 1 mM EDTA, 50 mM NaCl, 1.0 mM 2-mercaptoethanol, 0.1 mM each of dGTP, dCTP, dATP and dTTP and 5 units of Klenow fragment for 30 minutes at room temperature. The reaction was stopped by incubation at 65° for 10 minutes. The reaction mix was extracted once with phenol, twice with chloroform and precipitated with ethanol. Finally, the ethanol precipitated DNA was cleaved (in 50 ul of 25 mM Tris-HCl, pH 7.5, 10 mM MgCl₂, 25 mM NaCl) with 25 units of BamHl (37° for 1 hour). The resulting approximately 600 base pair fragment containing the aTCGF coding region was isolated by agarose gel electrophoresis and designated aTCGF segment BE.

Step B: Preparation of Transfer (Expression) Vector pEVPL-aTCGF

As shown in FIG. 7, the plasmid pEVPL (100 ug) in 250 ul of 25 mM Tris.HCl, pH 7.5, 10 mM MgCL₂ and 25 mM NaCl, prepared as in Example A, below, was digested with 100 units of KpnI at 37° for 1 hour. KphI cleaves pEVPL once, immediately adjacent to the cII start codon as depicted in the description above. The resulting 3' GTAC overhang is trimmed back to the blunt-ended G-C base pair terminal of the ATG codon by treating the KpnI cleaved pEVPL (100 ug) with 5 units of the Klenow fragment of DNA polymerase I in 100 ul of 10 mM Tris.HCl, pH 7.5, 10 mM MgCL₂ and 100 uM each of dATP, dCTP, dGTP and DTTP for 30 minutes at room temperature. The reaction was stopped by extraction with phenol then twice with chloroform and the DNA was collected by precipitation with ethanol. Finally, to create a cohesive end for easy cloning, the blunted DNA was cleaved with the restriction enzyme BamHI (100 ug of DNA in 100 ul of 25 mM Tris.HCl, pH 7.5, 10 mM MgCl₂, 25 mM NaCl with 100 units of BamHI) for 1 hour at 37°. The resulting vector fragment was purified by agarose gel electrophoresis and 50 ng of said vector fragment was then ligated to 100 ng of the 600 base pair of aTCGF coding region fragment (aTCGF Segment BE) in 10 ul of 10 mM Tris.HCl, 10 mM MGCl₂, 1 mM ATP, 1 mM dithiotreitol with 0.5 units of T4 ligase overnight at 16° C. The ligation mix was used to transform E. coli strain W3110-lambda Y139. Colonies which contained the desired pEVPL-aTCGF recombinant were identified by hybridization with the ³²P-labelled 17 mer. The recombinant plasmids from several such clones were analyzed by DNA sequencing to confirm that the first ATG of the CII gene in the pEVPL had been exactly fused to the first codon of mature aTCGF (the GCA for Ala-21).

Step C: Expression of the pEVPL-aTCGF in Bacteria

About 100 ml of W3110 lambda 139 pEVPL-aTCGF were grown to a density of 10⁹ cells per ml at 30° C. in broth for two hrs. The temperature was shifted to 38° C. for one hr. The cells were harvested by centrifugation (5 minutes at 5000 xg). The cell pellet was resuspended in 5 ml of 50 mM Tris-HCl, pH 7.5, 1 mM EDTA, 10 mM 2-mercaptoethanol and the cells were disrupted by sonication. Analysis of this cell extract by SDS polyacrylamide gel electrophoresis (15% polyacrylamide gel) indicated that 5–10% of the total cellular protein was aTCGF. Bioassay of this material showed that the extract contained at least 10,000 units per ml of activity indicating that the engineered microorganisms can be used to efficiently product a protein (aTCGF) having T-cell Growth Factor activity. Since assay of the sonicated extracts showed most of the aTCGF protein to be insoluble in the cytoplasm, the insoluble active protein was further concentrated by centrifugation, washing the pellet with acqueous buffer (10 mM Tris HCl, pH 7.5, and 1 mM EDTA) and dissolving it in SDS (0.1%). About 60% of the resulting protein product was expression product and was fractionated by preparative SDS gel electrophoresis and cutting out and eluting the band corresponding to a protein standard of known and similar molecular weight. About 90% of the eluted protein was expression protein product which was sequenced using a gas-phase microsequentor. In this manner it was found that about 25–40% of the expression product conformed to the 133 amino acid sequence of aTCGF (Table A, above), while the balance of 60–75% was the incompleted processed precursor of 134 amino acids beginning with Met-Ala-Pro-Thr (amino acids 20-133 in Table A above). The specific activity of this mixture of human aTCGF proteins is similar to that of the human T-Cell Growth Factor having the acid sequence known from Taniguchi et al, above, which had been expressed in an identical fashion.

EXAMPLE A

Preparation of plasmid pEVPL: The constructing of the plasmid pEVPL is represented in FIG. 8. Employed as a starting material was the plasmid pKC30cII which is described by Shimatake and Rosenberg, Nature, 292 (1981), pages 128–132 and also discussed by Maniatis et al, Molecular Cloning, A Laboratory Manual, Cold Spring Harbor Laboratory, 1982, Chapt 12, pages 404–433, the disclosure of both said publications being incorporated herein by reference as to the structure and properties of pKC30cII to the extent not described herein. The plasmid includes sequentially downstream from its $P_L$ promoter-operator an anti-termination recognition site (Nut L), the N gene region (N/2), an anti-termination recognition site (Nut R), the transcription termination signal (tR1), the cII gene region comprising its ribosome binding site sequence (RBSS) and coding sequence preceded by its ATG translation initiator, half of the O gene region (O/2) and the transcription termination signal (tL), all variously depicted in FIG. 8. The plasmid pKC30cII (10 μg) is first digested with 20 units of the endonuclease BamHI in 100 μl of 25 mM Tris, pH 8, 10 mM MgCl$_2$, 10 mM 2-mercaptoethanol, 50 mM NaCl and 100 μg/ml BSA for 1 hour at 37° to obtain after extraction (phenol/chloroform and twice with chloroform and ethanol precipitation) the linearized plasmid (shown in FIG. 8). The objective was then to cut back from the BamHI terminus approximately 1000 b.p. to reach the ATG translation initiation codon for the protein coded for by the cII coding sequence. For this purpose 10 μg of the linearized plasmid was incubated with 1200 units of Exonuclease III in 200 μl. of Exo III buffer (composed of 50 mM Tris, pH 8, 10 mM 2-mercaptoethanol and 5 mM MgCl$_2$) at 30° C. Aliquots (of 65 μl) were removed at 6, 7 and 8 minutes on the expectation that the condition of treatment removed about 150 bases/minute. The aliquots were combined in a tube containing 100 μl of 40 mM EDTA and 1M NaCl, and ethanol precipitated. The resulting combined 3' degraded DNA segments were then incubated with 80 units of Nuclease S1 in 320 l of S1 buffer (composed of 30 mM NaAc, pH 4.6, 200 mM NaCl and 1 mM ZnSO$_4$) for 30 minutes at 30°, in order to substantially remove the extensive 5' overhangs remaining from the Exo III treatment. The action of the Nuclease S1 was stopped by the addition of 40 μl of 0.5M Tris-HCl, pH 8.0, and 1M NaCl and the resulting DNA collected by ethanol precipitation after extraction with phenol/chloroform and chloroform. The resulting DNA segments were then blunt ended by incubating in 100 μl of 10 mM Tris HCl pH 7.5, 100 uM each dATP, dCTP, dGTP, and TTP, 1 mM dithiothreitol 10 mM MgCL$_2$ and 5 units of the Klenow fragment of DNA polymerase I for 15 min. to 37°. The reaction was stopped by addition of NaCl to 0.2M, and the mix was extracted with phenol/chloroform and several times with chloroform and the DNA collected by ethanol precipitation. The above reactions produce from each aliquot a multiplicity of different length segments represented by the three segments shown in FIG. 8. The subsequent treatments described below are represented in FIG. 8 only by the single desired segment in order to show more detail. The resulting blunt ended DNA segments were ligated to a unique BamHI adaptor prepared from a 10 mer and a 14 mer and having the sequence:

said adaptor being phosphorylated using ATP and T4 polynucleotide kinase as described for BamHI adaptors on page 5 of the M13 Cloning Dideoxy Sequencing Manual, supra. In addition to providing a BamHI cohesive end, this adaptor begins with 5 of the 6 nucleotides necessary for a KpnI site and will create said site when ligated to the ATG codon of the cII sequence. The adaptor 30 p mole) was therefore ligated to the blunt end DNA by incubating the 60 ul of 25 mM Tris HCl pH 7.5, 10 mM MgCl$_2$, 10 mM dithiotreitol (DTT) 100 uM ATP and 0.2 units of T4 ligase at 15° for 90 minutes. The reaction was stopped by heating to 68° for 15 minutes. The resulting DNA segments with their unique Kpn-BamHI adaptors (Kpn-BA) are represented in FIG. 8. The DNA from the adaptor ligation was diluted to 100 ul and NaCl added to a final concentration of 0.1M. This reaction mix was incubated with the endonuclease EcoRI (20 units) for 60 minutes at 37°. The reaction mix was extracted with phenol/chloroform, chloroform, ethanol precipitated and electrophoresed through a 1% Tris acetate agarose gel. The gel purified DNA segments in the size class of 2500 to 3000 b.p. were isolated from the gel using the glass powder protocol.

A pBR322 plasmid segment was prepared by digesting pBR322 DNA (10 μg) sequentially with the endonuclease BamHI (20 units) for 1 hour at 37° in 100 μl of BamHI Buffer (10 mM Tris-HCl, pH 7.5, 50 mM NaCl, 1 mM DTT), then raising the NaCl concentration to 0.1M and cutting with the endonuclease EcoRI. The reaction was stopped by extraction with phenol/chloroform and extracted twice with chloroform and ethanol precipitated. The 3985 base pair vector fragment was purified by electrophoresis through a Tris acetate gel followed by glass powder isolation of the DNA.

The above prepared pBR322 plasmid segment (50 ng) was then ligated with 25 ng of the selected gel purified DNA segments (2500–3000 b.p.) in a reaction mix (25 ul) containing 25 mM Tris-HCl, pH 7.5, 10 mM MgCl$_2$, 10 mM DTT, 100 uM ATP, and 0.1 units of T4 ligase (at 15° overnight). This reaction was used to transform E. coli W3110 lambda Y139 which carries a temperature sensitive lambda repressor protein (on a lambda lysogen in the bacterial chromosome) which can be used to shut off the $P_L$ promoter. The transformation was performed by incubating 10 ul of the ligation with 200 ul of transformation competent bacteria (CaCl$_2$ shocked) for 30 minutes on ice, 2 minutes @ 37°, then 30 minutes at 30° after diluting to 1 ml with L broth. The transformed bacteria were spread directly onto 4 nitrocellulose filters on L-broth containing agar plates having 25 mg/ml ampicillin. After incubation overnight at 30°, 2 replicas were amplified by incubation overnight on L Broth agar plates containing 100 mg/ml chloramphenicol. The filters were prepared for colony hybridization by standard treatment with base. One set of filters was probed overnight at room temperature with 100,000 CPM/ml of the 14 mer from the adaptor which had been $^{32}$P-labelled. The other set of filters were hybridized to a junction oligonucleotide which spans the junction of the adaptor to the ATG of the cII sequence and which is a 14 mer having the sequence:

ACATATGGTACCTA wherein the ACATATG is the sequence leading up to the first ATG of the cII sequence and GTACCTA is the start of the BamHI adaptor. Several colonies which hybridized to both probes were used to analytical amounts prepare plasmid DNA (rapid prep. method). The DNA's were tested for the presence of a single BamHI site and a single Kpn I site. One such plasmid was further checked by Maxam-Gilbert sequencing (labeled by the T4 kinase reaction at the BamHI site), and found to have the desired sequence. This plasmid was designated pEVPL.

EXAMPLE B

Expression of aTCGF in pEVPL-aTCGF in $^{35}$S-Met labelled *E. Coli* W3110 Lambda Y139

*E. Coli* W3110 λ139 (10 ml) which has been transformed with pEVPL-aTCGF is grown overnight at 30°. in M63 medium and 5% L-Broth in the presence of 25 μg/ml of ampicillin. The cells are then subcultured at 30° for 2 hours after dilution 1:50 in M63 medium plus ampicillin. The temperature of the cell mass is then raised to 42° for 10 minutes, cooled to 37° and the cells labelled with $^{35}$S-methionine (20 μcuries/ml) for 2–3 minutes, followed by chasing with 300 μl of cold methionine (0.5%) per each 5 ml of culture. Aliquots (0.5–1.0 ml) are collected at several different time intervals after labelling, e.g. 10, 30, 60, 120 and 150 minutes. Each aliquot sample is prepared by collecting the cells (5 minute spin in microfuge) and resuspending in 100 μl SDS gel sample buffer (25 mM Tris-HCl, ph 6.8, 2% SDS, 20% glycerol, 0.002% bromophenol blue and 100 mM 2-mercaptoethanol). The proteins from the samples are then fractionated on a 15% polyacrylamide SDS gel in accord with the method described by Laemmli, Nature 227, page 680 (1970). In this manner it was confirmed that expression of pEVPL-aTCGF in *E. Coli* W3110 lambda Y139 produces good quantities of a protein product having the ca 15,000 Dalton molecular weight of TCGF. In this Example B the M63 medium is prepared by mixing 100 ml of a sterilized 1:5 water dilution of a 1 liter aqueous mixture of 15 g. KH$_2$PO$_4$, 35 g. K$_2$HPO$_4$, 10 g. (NH$_4$)$_2$SO$_4$ and 2.5 ml FeSO$_4$ (1 mg/ml) with sterilized mixture of 10 ml of 20% glucose and 1 ml 1M MgSO$_4$.

While the invention has been described with reference to certain particular embodiments, it will be evident that numerous modifications may be made as a result of and within the scope of the invention, and in the practicing thereof, including but in no way limited to, modifications in vectors, transfer vectors, probes, cell systems and microorganisms for expression, and in procedures for construction and analysis, all as evident to those skilled in the art. Among these large number and variety of modification is the modification of a transfer vector for bacterial expression, e.g., the pEVPL-aTCGF, to insert by known procedures a sequence for resistance to the antibiotic neomicin as might be preferred in some manufacturing situation. Similarly, in view of the variability of the genetic code, the cDNA sequence coding for aTCGF may be modified, e.g. by the known process of site specific mutagenesis, to produce a different sequence of nucleotides coding for the same aTCGF protein.

What is claimed is:

1. A cDNA sequence coding for an IL-2 protein characterized by a serine at amino acid position 45, said DNA sequence comprising the sequence

```
        21
     Ala Pro Thr Ser Ser Ser Thr Lys Lys
5'   GCA CCT ACT TCA AGT TCT ACA AAG AAA

30
     Thr Gln Leu Gln Leu Glu His Leu Leu Leu
     ACA CAG CTA CAA CTG GAG CAT TTA CTT CTG 40                45
     Asp Leu Gln Met Ile Ser Asn Gly Ile Asn
     GAT TTA CAG ATG ATT TCG AAT GGA ATT AAT

50
     Asn Tyr Lys Asn Pro Lys Leu Thr Arg Met
     AAT TAC AAG AAT CCC AAA CTC ACC AGG ATG

60
     Leu Thr Phe Lys Phe Tyr Met Pro Lys Lys
     CTC ACA TTT AAG TTT TAC ATG CCC AAG AAG

70
     Ala Thr Glu Leu Lys His Leu Gln Cys Leu
     GCC ACA GAA CTG AAA CAT CTT CAG TGT CTA

80
     Glu Glu Glu Leu Lys Pro Leu Glu Glu Val
     GAA GAA GAA CTC AAA CCT CTG GAG GAA GTG

90
     Leu Asn Leu Ala Gln Ser Lys Asn Phe His
     CTA AAT TTA GCT CAA AGC AAA AAC TTT CAC

100
     Leu Arg Pro Arg Asp Leu Ile Ser Asn Ile
     TTA AGA CCC AGG GAC TTA ATC AGC AAT ATC

110
     Asn Val Ile Val Leu Glu Leu Lys Gly Ser
     AAC GTA ATA GTT CTG GAA CTA AAG GGA TCT

120
     Glu Thr Thr Phe Met Cys Glu Tyr Ala Asp
     GAA ACA ACA TTC ATG TGT GAA TAT GCT GAT

130
     Glu Thr Ala Thr Ile Val Glu Phe Leu Asn
     GAG ACA GCA ACC ATT GTA GAA TTT CTG AAC

140
     Arg Trp Ile Thr Phe Cys Gln Ser Ile Ile
     AGA TGG ATT ACC TTT TGT CAA AGC ATC ATC

150
                       Ser Thr Leu Thr
                       TCA ACA CTG ACT 3'
```

2. A transfer vector containing the cDNA sequence of claim 1.

3. The transfer vector according to claim 2 comprising pCVSVL-aTCGF or pEVPL-aTCGF.

4. A bacterial host cell transformed with the vector of claim 2.

5. A mammalian host cell transformed with the vector of claim 2.

* * * * *